US008808189B2

(12) United States Patent
Tokko et al.

(10) Patent No.: US 8,808,189 B2
(45) Date of Patent: Aug. 19, 2014

(54) BLOOD PRESSURE MEASUREMENT DEVICE INCLUDING CUFF TO BE WRAPPED AROUND MEASUREMENT SITE

(75) Inventors: Yoshihide Tokko, Kyoto (JP); Chisato Uesaka, Kyoto (JP); Yukiya Sawanoi, Nara (JP); Naomi Matsumura, Takatsuki (JP); Masaki Tomioka, Kyoto (JP); Reiji Fujita, Kyoto (JP); Shingo Yamashita, Kyoto (JP); Yuuichiro Tamaki, Kyoto (JP)

(73) Assignee: Omron Healthcare Co., Ltd., Kyoto (JP)

( * ) Notice: Subject to any disclaimer, the term of this patent is extended or adjusted under 35 U.S.C. 154(b) by 428 days.

(21) Appl. No.: 13/198,051

(22) Filed: Aug. 4, 2011

(65) Prior Publication Data

US 2011/0295130 A1 Dec. 1, 2011

Related U.S. Application Data

(63) Continuation of application No. PCT/JP2009/066236, filed on Sep. 17, 2009.

(30) Foreign Application Priority Data

Feb. 6, 2009 (JP) ................................ 2009-026390

(51) Int. Cl.
*A61B 5/02* (2006.01)
*A61B 5/0225* (2006.01)
*A61B 5/021* (2006.01)

(52) U.S. Cl.
CPC ........... *A61B 5/0225* (2013.01); *A61B 5/02255* (2013.01); *A61B 5/02141* (2013.01)
USPC ......................................................... 600/490

(58) Field of Classification Search
USPC ................................ 600/485, 490, 493, 494
See application file for complete search history.

(56) References Cited

U.S. PATENT DOCUMENTS

2005/0240109 A1 10/2005 Inoue et al.

FOREIGN PATENT DOCUMENTS

CN 1689508 A 11/2005
CN 101340845 A 1/2009

(Continued)

OTHER PUBLICATIONS

Office Action issued in corresponding Chinese Application No. 200980156359.5 dated Feb. 28, 2013, and English translation thereof (16 pages).
Patent Abstracts of Japan, Publication No. 2005-305028, Publication Date: Nov. 4, 2005, 1 page.

(Continued)

*Primary Examiner* — Navin Natnithithadha
*Assistant Examiner* — Etsub Berhanu
(74) *Attorney, Agent, or Firm* — Osha Liang LLP

(57) ABSTRACT

A blood pressure measurement device includes a wrapping strength detecting portion for detecting a wrapping strength of a cuff with respect to a measurement site. The wrapping strength detecting portion detects the wrapping strength of the cuff prior to calculation of a blood pressure value by a blood pressure calculation unit. That is, the wrapping strength of the cuff is detected based on a relationship indicated by a volume change ΔV12 of the cuff detected with a change in the detection pressure in the cuff wrapped around the measurement site from P1 to P2 and a volume change Δ23 of the cuff detected with change from P2 to P3 in a process of controlling the cuff pressure by a pressure adjustment unit.

22 Claims, 31 Drawing Sheets

(56) References Cited

FOREIGN PATENT DOCUMENTS

| | | | | |
|---|---|---|---|---|
| JP | 02-114934 | A | | 4/1990 |
| JP | 06-319707 | A | | 11/1994 |
| JP | 2005-305028 | A | | 11/2005 |
| JP | 4134234 | B1 | | 8/2008 |
| WO | WO 2007066461 | A1 | * | 6/2007 |
| WO | 2008/096741 | A1 | | 8/2008 |

OTHER PUBLICATIONS

Patent Abstracts of Japan, Publication No. 06-319707, Publication Date: Nov. 22, 1994, 1 page.

Patent Abstracts of Japan, Publication No. 02-114934, Publication Date: Apr. 27, 1990, 1 page.

International Search Report issued in PCT/JP2009/066236 mailed on Dec. 15, 2009, with English translation thereof, 6 pages.

* cited by examiner 1
10
Display unit
40
Gain table
391
Memory
39
Timing unit
43
100
CPU
Oscillation circuit
35
Pump drive circuit
36
Valve drive circuit
37
Power supply unit
42
Operation unit
41
25
Pressure sensor
32
Pump
33
Exhaust valve
34
24
Air bladder
21
Cuff
20

| ID (39E) | User (39F) | Measurement date and time (39G) | Blood pressure value / Pulse rate (39H) | Cuff wrapping strength (39I) | Measurement condition (39J) |
|---|---|---|---|---|---|
| 1 | A | yy/mm/dd hh:mm1 | SBP, DBP, PLS | OK | L |
| 2 | B | yy/mm/dd hh:mm2 | SBP, DBP, PLS | NG | M |
| ······ | ······ | ······ | ······ | ······ | ······ |

395

| Arm peripheral length (39K) | Threshold value (39L) |
|---|---|
| L | ThL($L\alpha q$, $L\beta q$) |
| M | ThM($M\alpha q$, $M\beta q$) |

396

| Arm peripheral length (39K) | Threshold value (39M) |
|---|---|
| L | $\Delta$PcL($L\alpha p$, $L\beta p$) |
| M | $\Delta$PcM($M\alpha p$, $M\beta p$) |

397

| Fluid amount (39N) | Arm peripheral length (39P) |
|---|---|
| $\Delta$QM | M |
| $\Delta$QL | L |

BLOOD PRESSURE MEASUREMENT DEVICE INCLUDING CUFF TO BE WRAPPED AROUND MEASUREMENT SITE

TECHNICAL FIELD

The present invention relates to blood pressure measurement devices, and in particular, to a blood pressure measurement device for detecting a wrapping strength of a cuff with respect to a measurement site.

BACKGROUND ART

A blood pressure is one index for analyzing a circulatory disease. Performing risk analysis based on the blood pressure is effective in preventing cardiovascular diseases such as stroke, heart failure, and cardiac infarction. Conventionally, diagnosis is made from the blood pressure (examination room blood pressure) measured in medical institutions such as at the time of hospital visits, health checks, or the like. However, it is found from researches of recent years that the blood pressure (home blood pressure) measured at home is more useful in the diagnosis of circulatory diseases than the examination room blood pressure. Accompanied therewith, over 30 million sphygmomanometers for use at home are widely used in the country.

In the conventional blood pressure measurement device, the cuff is wrapped around the measurement site of a living body in advance for blood pressure measurement, but it is difficult to define the appropriate wrapping strength because the extent of the wrapping strength, that is, pressurization of the wrapping on the living body is not known. Accordingly, patent document 1 (Japanese Unexamined Patent Publication No. 2005-305028 (Japanese Patent No. 3815487) describes a configuration of enclosing gas in the cuff in advance, and then automatically wrapping the cuff around the measurement site. Whether or not relative displacement of the pressure in the cuff in the process of wrapping around the measurement site reaches a predetermined level is detected to detect if the wrapping state is in an appropriate state for blood pressure measurement.

In patent document 2 (Japanese Unexamined Patent Publication No. 6-319707), the cuff compliance obtained from the relationship of the pressure in the cuff and the change in volume after wrapping the cuff around the measurement site is used to correct the amplitude of the pulse wave used in the blood pressure measurement process, so that highly accurate blood pressure measurement can be carried out without depending on the person to be measured or the wrapping strength of the cuff.

The sphygmomanometer of patent document 3 (Japanese Unexamined Patent Publication No. 2-114934) and patent document 4 (Japanese Patent Publication No. 4134234) starts the blood pressure measurement with the cuff wrapped around the measurement site, and determines the attachment state of the cuff with respect to the measurement site based only on the amount of change of the subsequent cuff pressure. Therefore, this procedure can also be applied to the blood pressure measurement device having a configuration in which the person to be measured wraps the cuff around the measurement site.

PRIOR ART DOCUMENT

Patent Document 1: Japanese Unexamined Patent Publication No. 2005-305028

Patent Document 2: Japanese Unexamined Patent Publication No. 6-319707

Patent Document 3: Japanese Unexamined Patent Publication No. 2-114934

Patent Document 4: Japanese Patent Publication No. 4134234

SUMMARY OF INVENTION

In patent document 1, air of a predetermined volume needs to be in the cuff in advance to determine the attachment state of the cuff. The cuff is thus formed to a cylindrical shape. The configuration of patent document 1 is effective in the sphygmomanometer for automatically wrapping around the measurement site while reducing the diameter of the cuff, but similar detection cannot be made with the sphygmomanometer in which the cuff in a planar state is wrapped around the measurement site by the person to be measured.

In patent document 2, highly accurate blood pressure measurement can be carried out without depending on the person to be measured or the wrapping strength of the cuff, but the wrapping strength is not detected. Therefore, if the person to be measured wraps the cuff around the measurement site, it is unclear whether or not the wrapping strength of the cuff is appropriate.

The sphygmomanometer of patent document 3 determines whether or not the cuff is attached to the measurement site, that is, whether or not the cuff has detached. To this end, only the cuff pressure is detected, and whether or not the cuff has detached is determined by the comparison result of the detected cuff pressure and the reference value. Therefore, the function of detecting the extent of the wrapping strength is not provided.

In the sphygmomanometer of patent document 4, only the cuff pressure is detected to determine the quality of the attachment state of the cuff. The detected cuff pressure and the reference value are compared to determine the quality of the attachment state of the cuff based on the comparison result. However, the change in cuff pressure during the blood pressure measurement is known to greatly change by the size (circumferential length) or quality (muscular or fattiness etc.) of the measurement site, the type of cuff (size etc.) and the ambient environment (room temperature etc.) in addition to the attachment state of the cuff. The reference value of patent document 4 is set without taking such factors into consideration, and hence, the attachment state cannot be accurately detected.

Therefore, one or more embodiments of the present invention provides a blood pressure measurement device for accurately detecting the wrapping strength of the cuff at the measurement site.

According to one or more embodiments of the present invention, a blood pressure measurement device includes a cuff to be wrapped around a measurement site of a blood pressure, a pressure control unit for controlling a cuff pressure in the cuff wrapped around the measurement site, a pressure detection unit for detecting the cuff pressure, a volume detection unit for detecting volume of the cuff in the process of pressurizing or depressurizing the cuff pressure by the pressure control unit, a blood pressure calculation unit for calculating a blood pressure value in the process of pressurizing or depressurizing the cuff pressure by the pressure control unit, and a wrapping strength detecting portion for detecting a wrapping strength of the cuff with respect to the measurement site.

The wrapping strength detecting portion detects the wrapping strength of the cuff based on a pressure-volume change relationship according to a change of the cuff pressure detected in the cuff wrapped around the measurement site and a volume change of the cuff detected by the volume detection unit with change of the cuff pressure in the process of controlling the cuff pressure by pressurization or depressurization by the pressure control unit.

According to one or more embodiments of the present invention, the wrapping strength detecting portion detects the wrapping strength of the cuff based on a pressure-volume change relationship and a measurement condition, and the pressure-volume change relationship indicates a relationship of the amount of change of the cuff pressure and the amount of change of the volume when at least one of the cuff pressure and the volume detected in the cuff wrapped around the measurement site is changed at a predetermined amount in the process of controlling the pressure by pressurization or depressurization by the pressure control unit.

According to one or more embodiments of the present invention, the predetermined amount is changed based on the measurement condition.

According to one or more embodiments of the present invention, the measurement condition indicates a circumferential length of the measurement site.

According to one or more embodiments of the present invention, the measurement condition is a factor that changes the pressure-volume relationship, where the factor indicates one or more of a circumferential length of the measurement site, a quality of the measurement site, a size of the cuff, temperature and humidity around the blood pressure measurement device, characteristics of the pressure control unit, as well as a fluid volume remaining in the cuff at the end of the blood pressure measurement.

According to one or more embodiments of the present invention, the measurement condition is detected based on the pressure-volume change relationship of the cuff.

According to one or more embodiments of the present invention, the blood pressure measurement device further includes a reception unit for receiving the measurement condition.

According to one or more embodiments of the present invention, the blood pressure measurement device outputs the wrapping strength detected by the wrapping strength detecting portion and the measurement condition in association to each other.

According to one or more embodiments of the present invention, the blood pressure measurement device outputs the measurement condition.

According to one or more embodiments of the present invention, the blood pressure calculation unit calculates the blood pressure value based on a volume pulse wave signal and a parameter value, and changes the parameter value based on at least one of the wrapping strength and the measurement condition.

According to one or more embodiments of the present invention, the magnitude of the amplitude of the volume pulse wave signal for calculating the blood pressure value is changed based on the wrapping strength detected by the wrapping strength detecting portion.

According to one or more embodiments of the present invention, the pressure control unit controls the cuff pressure according to control data. The control data is changed based on at least one of the wrapping strength and the measurement condition.

According to one or more embodiments of the present invention, the blood pressure measurement device cancels the blood pressure measurement when the detected wrapping strength does not indicate an appropriate level.

According to one or more embodiments of the present invention, the blood pressure measurement device pauses the measurement operation of the blood pressure after the wrapping strength of the cuff is detected.

According to one or more embodiments of the present invention, the wrapping strength detecting portion detects the wrapping strength of the cuff based on a pressure-volume change relationship indicated by a volume change of the cuff detected with change of the cuff pressure detected in the cuff wrapped around the measurement site from a first value to a second value and a volume change of the cuff detected with change from the second value to a third value in a process of controlling the cuff pressure by pressurization or depressurization by the pressure control unit.

According to one or more embodiments of the present invention, the wrapping strength detecting portion determines whether or not a predetermined condition for determining the wrapping strength is satisfied based on the pressure-volume change relationship, and detects the wrapping strength of the cuff based on the determination result.

According to one or more embodiments of the present invention, the blood pressure calculation unit calculates the blood pressure value based on a volume pulse wave signal and a parameter value, and changes the parameter value based on the wrapping strength.

According to one or more embodiments of the present invention, the blood pressure measurement device changes the magnitude of the amplitude of the volume pulse wave signal for calculating the blood pressure value based on the wrapping strength detected by the wrapping strength detecting portion.

According to one or more embodiments of the present invention, the pressure control unit controls the cuff pressure according to control data. The control data is changed based on the wrapping strength.

According to one or more embodiments of the present invention, the pressure control unit includes a pressure adjustment unit for supplying or discharging fluid of a constant amount per unit time with respect to the cuff to control the cuff pressure. The wrapping strength detecting portion includes a relationship detecting portion for detecting the pressure-volume change relationship.

The relationship detecting portion detects the pressure-volume change relationship based on a relationship of an elapsed time for supplying or discharging the fluid with respect to the cuff by the pressure adjustment unit, and the pressure detected with elapse of time.

According to one or more embodiments of the present invention, the elapsed time is substituted by a parameter value for determining the elapsed time.

According to one or more embodiments of the present invention, the pressure adjustment unit is an actuator having a rotation mechanism. The elapsed time is substituted by a rotation number of the actuator.

According to one or more embodiments of the present invention, the elapsed time refers to a power amount consumed by the pressure adjustment unit.

According to one or more embodiments of the present invention, the elapsed time is substituted by a supply amount or a discharge amount of the fluid.

According to one or more embodiments of the present invention, the blood pressure measurement device outputs the wrapping strength detected by the wrapping strength detecting portion to outside.

According to one or more embodiments of the present invention, the wrapping strength detecting portion detects the wrapping strength of the cuff with respect to the measurement site when a predetermined instruction is made.

The wrapping strength detecting portion detects the wrapping strength of the cuff based on the pressure-volume change relationship according to the change in cuff pressure detected in the cuff wrapped around the measurement site and the volume change of the cuff detected by the volume detection unit with change of the cuff pressure in the process of controlling the cuff pressure by pressurization or depressurization by the pressure control unit.

According to one or more embodiments of the present invention, the wrapping strength of the cuff wrapped around the measurement site can be detected.

BRIEF DESCRIPTION OF THE DRAWINGS

FIG. 18 is a view showing a storage content of a memory according to the second embodiment.

DETAILED DESCRIPTION OF INVENTION

Figure 1:
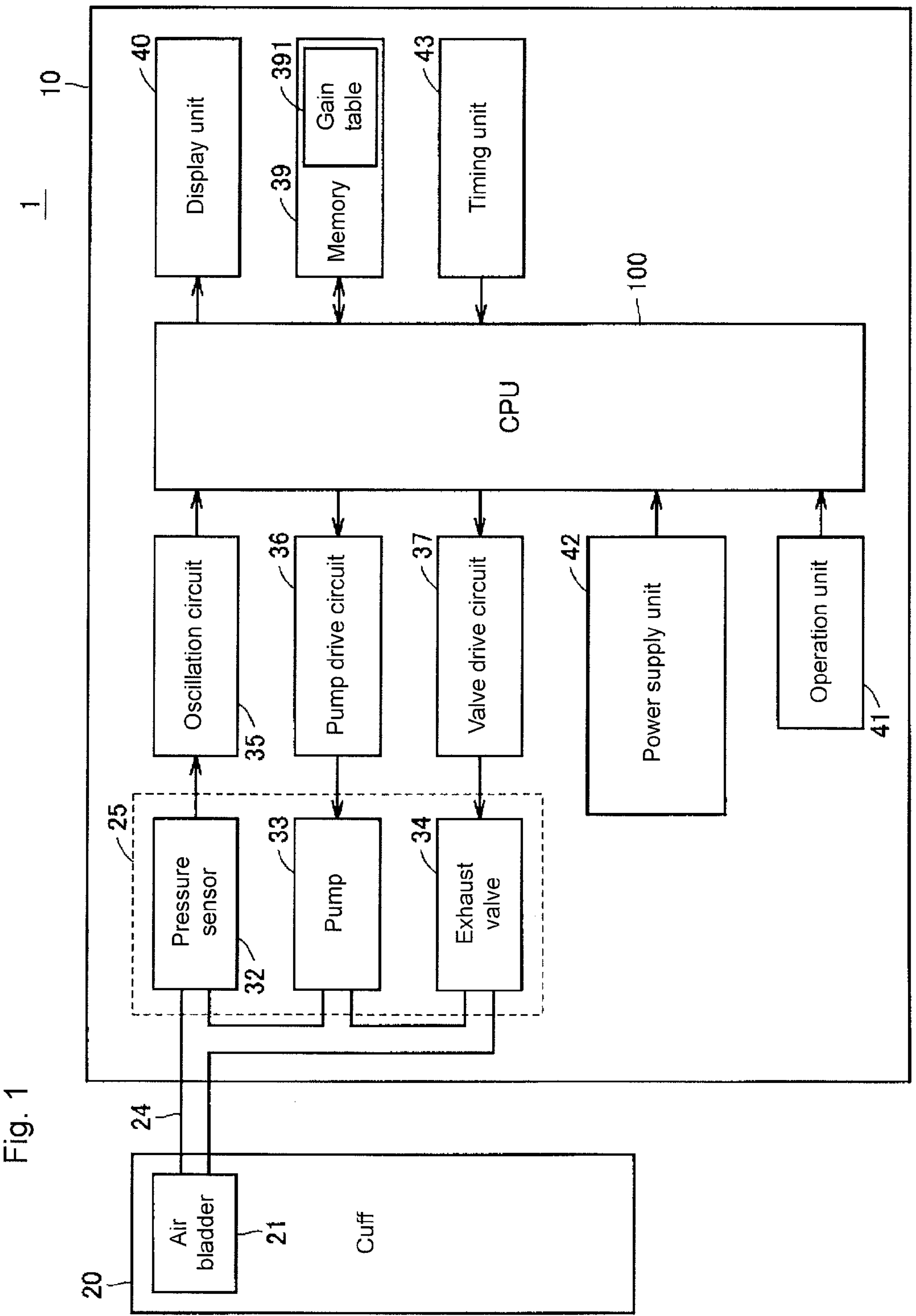
FIG. 1 is a hardware configuration diagram of a blood pressure measurement device according to a first embodiment.

Each embodiment of the present invention will be hereinafter specifically described with reference to the drawings. In each figure, the same reference numeral refers to the same or corresponding portion, and the description thereof will not be repeated.

First Embodiment (Blood Pressure Measurement Device)

Figure 2:
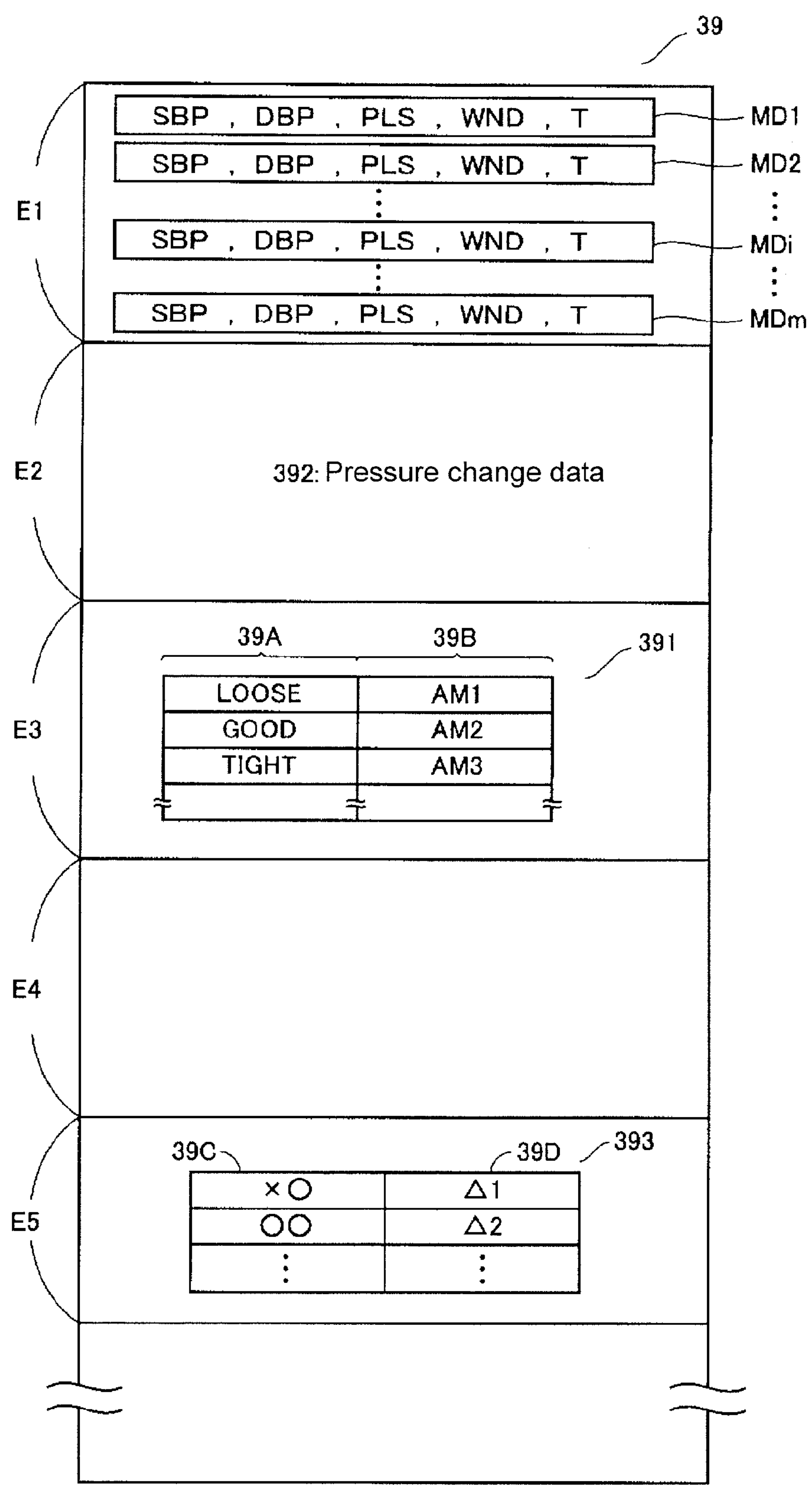
FIG. 2 is a view showing an example of a storage content of a memory according to the first embodiment.
Figure 3:
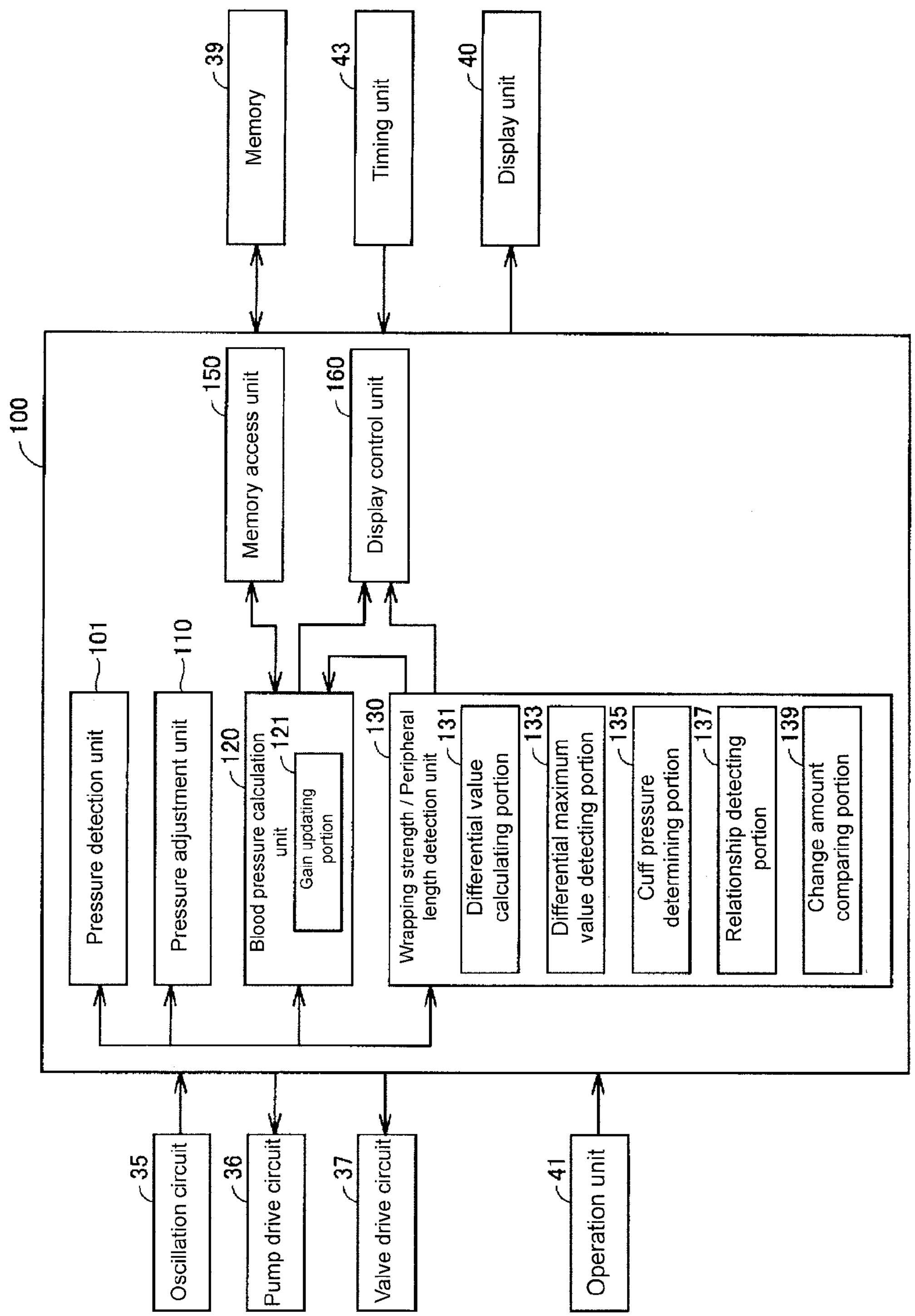
FIG. 3 is a function configuration diagram of the blood pressure measurement device according to the first embodiment.
Figure 4:
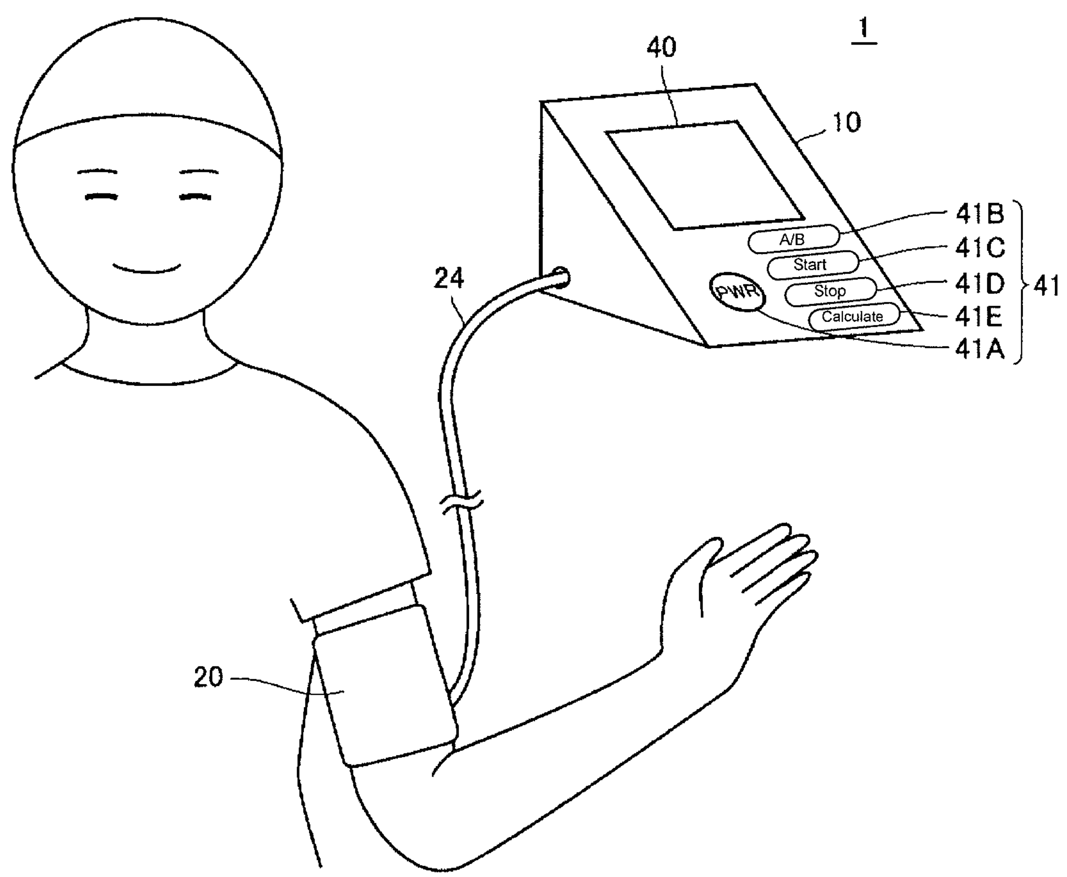
FIG. 4 is a view showing an outer appearance and a usage mode of the blood pressure measurement device according to the first embodiment.

FIG. 1 shows a hardware configuration of a blood pressure measurement device 1 according to the present embodiment, FIG. 2 shows an example of a content of a memory 39 of FIG. 1, FIG. 3 shows a function configuration of the blood pressure measurement device 1, and FIG. 4 schematically shows the usage mode at the time of the blood pressure measurement of the blood pressure measurement device 1 along with the outer appearance of the device.

(Outer Appearance)

With reference to FIG. 1 and FIG. 4, the blood pressure measurement device 1 includes a main body 10, a cuff 20 to be wrapped around a measurement site of a person to be measured such as an upper arm, and an air tube 24 for connecting the main body 10 and the cuff 20.

A display unit 40 for displaying measurement results, or the like, and an operation unit 41 for accepting input of an instruction from a user (representatively, person to be measured) are arranged on a surface of the main body 10. The operation unit 41 includes, for example, a switch 41A for switching ON/OFF of a power supply, a switch 41B operated to identify the person to be measured, a switch 41C and a switch 41D for inputting instructions to start and stop the measurement, and a switch 41E for inputting instruction to read out and display past measurement results.

The display unit 40 is configured by a display such as liquid crystal.

The air tube 24 is connected to a side surface of the main body 10.

The cuff 20 is a band-shaped bag having a substantially rectangular shape as shown in FIG. 1, and includes an air bladder 21 in the bag. When wrapping the cuff 20 around the measurement site as shown in FIG. 4, the side extending in the longitudinal direction of the cuff 20 is to lie along the circumference (arm circumference) of the measurement site. The cuff 20 has a cylindrical shape that lies along the circumference of the measurement site when the wrapping is completed. If the cuff 20 is appropriately wrapped around the measurement site in such state, the arm circumferential length and the length of the circumference of the cross-section of the cylinder become substantially equal, and a "good" wrapped state in which the pressurization with respect to the measurement site is an appropriate level for blood pressure measurement is obtained. If the length of the circumference is short with respect to the arm circumferential length, the cuff 20 is tightly wrapped around the measurement site, and a "tightly" wrapped state in which the pressurization with respect to the measurement site is higher than the appropriate level is obtained. If the length of the circumference is long, the cuff 20 is loosely wrapped around the measurement site, and a "loosely" wrapped state in which the pressurization with respect to the measurement site is lower than the appropriate level is obtained.

If the blood pressure measurement is started in the "tightly" wrapped state or the "loosely" wrapped state, the artery of the measurement site cannot be appropriately pressurized, and the accuracy of the blood pressure measurement cannot be obtained. Therefore, the "good" wrapped state in which the artery can be appropriately pressurized by the inner pressure of the cuff 20 is required to obtain the measurement accuracy.

(Hardware Configuration)

With reference to FIG. 1, the cuff 20 of the blood pressure measurement device 1 includes the air bladder 21 including air. The air bladder 21 is connected to an air system 25 incorporated in the main body 10 through the air tube 24.

The air system 25 includes a capacitance pressure sensor 32 for detecting pressure (hereinafter referred to as "cuff pressure") in the air bladder 21, a pump 33 for supplying air to the air bladder 21, and an exhaust valve 34 opened and closed to exhaust or enclose the air of the air bladder 21.

The main body 10 incorporates a CPU (Central Processing Unit) 100 for intensively controlling and monitoring each unit, a nonvolatile memory 39, a display unit 40, an operation unit 41, a power supply unit 42, and a timing unit 43 for timing time. The main body 10 also includes an oscillation circuit 35, a pump drive circuit 36 for driving the pump 33, and a valve drive circuit 37 for driving the exhaust valve 34 in relation to the air system 25.

The pump drive circuit 36 controls the drive of the pump 33 based on a control signal provided from the CPU 100. The valve drive circuit 37 performs an open/close control of the exhaust valve 34 based on the control signal provided from the CPU 100.

The capacitance value of the pressure sensor 32 changes according to the cuff pressure. The oscillation circuit 35 outputs a signal of an oscillating frequency corresponding to the capacitance value of the pressure sensor 32 to the CPU 100. The CPU 100 converts the signal obtained from the oscillation circuit 35 to pressure, and detects pressure.

The power supply unit 42 supplies power to the CPU 100 according to an instruction of power supply ON from the operation unit 41.

The memory 39 stores program for causing the CPU 100 to perform a predetermined operation and various types of information such as measurement result information.

(Example of Storage Content)

With reference to FIG. 2, the memory 39 includes a storage region E1 of a blood pressure measurement result, a storage region E2 for storing pressure change data 392 written by a wrapping strength/circumferential length detection unit 130, to be described later, a storage region E3 for storing a table 391 in which data of a gain for increasing or decreasing the amplitude level of the volume pulse wave component is stored, a storage region E4 serving as a temporary storage region and a work region of the data, and a storage region E5 for storing a table 393 searched to detect the circumferential length of the measurement site. In the storage region E1 of the blood pressure measurement result, the measurement data MDi (i=1, 2, 3, . . . , m) for every blood pressure measurement is stored in units of records. The measurement data MDi includes systolic blood pressure data SBP indicating a maximum blood pressure (systolic blood pressure), minimum blood pressure data DBP indicating a minimum blood pressure (diastolic blood pressure), pulse rate data PLS indicating a pulse rate, strength data WND indicating a detected wrapping strength with respect to the measurement site of the cuff 20, and measurement time data T indicated by the timing unit 43. The storage form of the measurement result is not restrictive.

The details of the pressure change data 392 stored in the storage region E2 will be described later.

The data of the table 391 of the gain stored in the storage region E3 is the data detected in advance through experiments based on the data sampled from a great number of subjects. Specifically, data 39A indicating the wrapping strength of the cuff 20 detected by the wrapping strength/circumferential length detection unit 130, and gain data 39B referenced to determine the gain of the volume pulse wave component detected in the blood pressure measurement in correspondence with each data 39A are stored. The gain data 39B refers to a value for amplifying (larger) or attenuating (smaller) the amplitude of the volume pulse wave component detected when the blood pressure measurement is performed in the corresponding wrapping strength so as to become the amplitude level for normal blood pressure measurement (when wrapped with normal strength (e.g., when detected as "good" wrapping)).

The storage region E4 is used as a work region for data processing where the data for processing is temporarily stored at the time of the blood pressure measurement or at the time of the detection of the wrapping strength of the cuff 20.

The data of the table 392 stored in the storage region E5 is the data detected in advance through experiments based on the data sampled from a great number of subjects. Specifically, data 39C indicating a value of pressure volume change index ΔP23/ΔV23 (to be described later) calculated when the wrapping strength/circumferential length detection unit 130 detects the wrapping strength of the cuff 20, and data 39D of the circumferential length of the measurement site corresponding to each data 39C are stored.

(Function Configuration)

FIG. 3 shows function blocks of the blood pressure measurement device according to the present embodiment. In FIG. 3, the illustration of the hardware that does not directly exchange signals with the CPU 100 is omitted.

With reference to FIG. 3, the CPU 100 includes a pressure detection unit 101, a pressure adjustment unit 110, a blood pressure calculation unit 120, the wrapping strength/circumferential length detection unit 130, a memory access unit 150 for accessing data of the memory 39, and a display control unit 160 for controlling the display of the display unit 40.

The pressure detection unit 101 inputs the output signal of the oscillation circuit 35, detects the oscillating frequency of the input signal, and converts the detected oscillating frequency to a pressure value signal. The pressure detection unit 101 includes an HPF portion for extracting a volume pulse wave signal by performing an HPF (High Pass Filter) process on the pressure value signal and outputting the same, and an LPF portion for extracting a pressure absolute value signal (hereinafter referred to as a cuff pressure signal) by performing an LPF (Low Pass Filter) process on the pressure value signal and outputting the same.

The pressure adjustment unit 110 adjusts the cuff pressure of the cuff 20 by controlling the operation of the pump drive circuit 36 and the valve drive circuit 37.

The blood pressure calculation unit 120 inputs the volume pulse wave signal extracted by the HPF portion of the pressure detection unit 101 and processes the input volume pulse wave signal according to a predetermined procedure to calculate the maximum blood pressure (systolic blood pressure) and the minimum blood pressure (diastolic blood pressure), and also calculates the pulse rate according to a well known procedure. The procedure for calculating the blood pressure is performed according to the oscillometric method or the like.

The blood pressure calculation unit 120 includes a gain updating portion 121. The gain updating portion 121 selectively updates the gain of the volume pulse wave signal extracted by the HPF portion of the pressure detection unit 101 based on the strength (loose, good, tight) of wrapping of the cuff 20 with respect to the measurement site detected by the wrapping strength/circumferential length detection unit 130. Specifically, the gain table 391 of the memory 39 is searched through the memory access unit 150 based on the detected wrapping strength. The data 39B of the gain stored in the gain table 391 is read out in correspondence with the wrapping strength through the search, and the gain of the volume pulse wave signal, which the blood pressure calculation unit 120 uses to calculate the blood pressure, is updated by the read data 39B of the gain.

The wrapping strength/circumferential length detection unit 130 includes a differential value calculating portion 131 for inputting a cuff pressure signal indicating the cuff pressure detected according to time series from the LPF portion of the pressure detection unit 101 and performing a differential calculation process on the waveform to calculate the differential value, a differential maximum value detecting portion 133 for detecting a maximum value of the calculated differential value, a cuff pressure determining portion 135, a relationship detecting portion 137, and a change amount comparing portion 139.

The cuff pressure determining portion 135 determines whether or not the cuff pressure satisfies a predetermined condition based on the cuff pressure signal. The relationship detecting portion 137 calculates the amount of change of the cuff pressure. The change amount comparing portion 139 compares the two cuff pressure change amounts calculated by the relationship detecting portion 137.

(Principle of Detecting Wrapping Strength)

Figure 5:
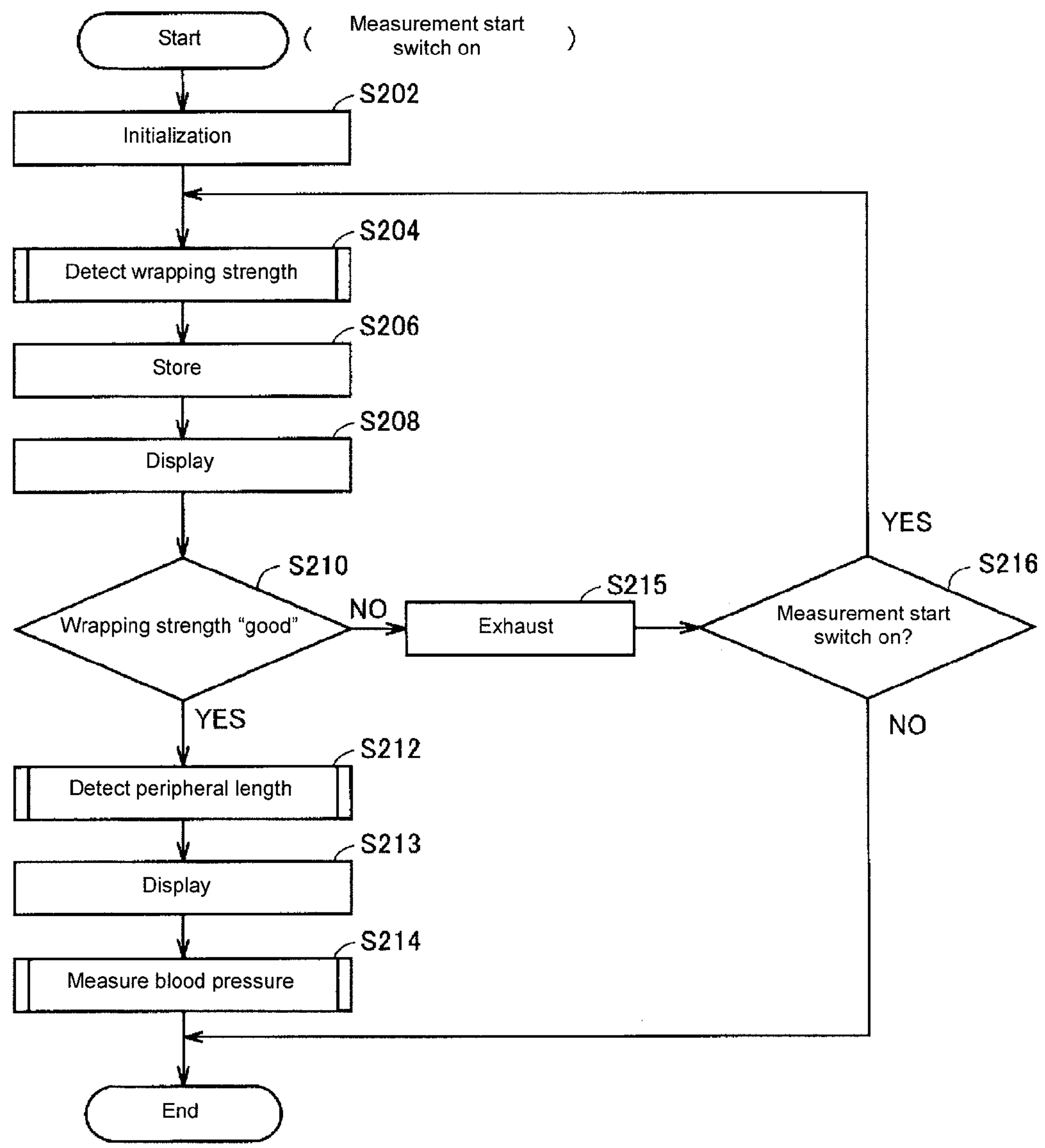
FIG. 5 is an overall flowchart of a measurement process according to the first embodiment.
Figure 6:
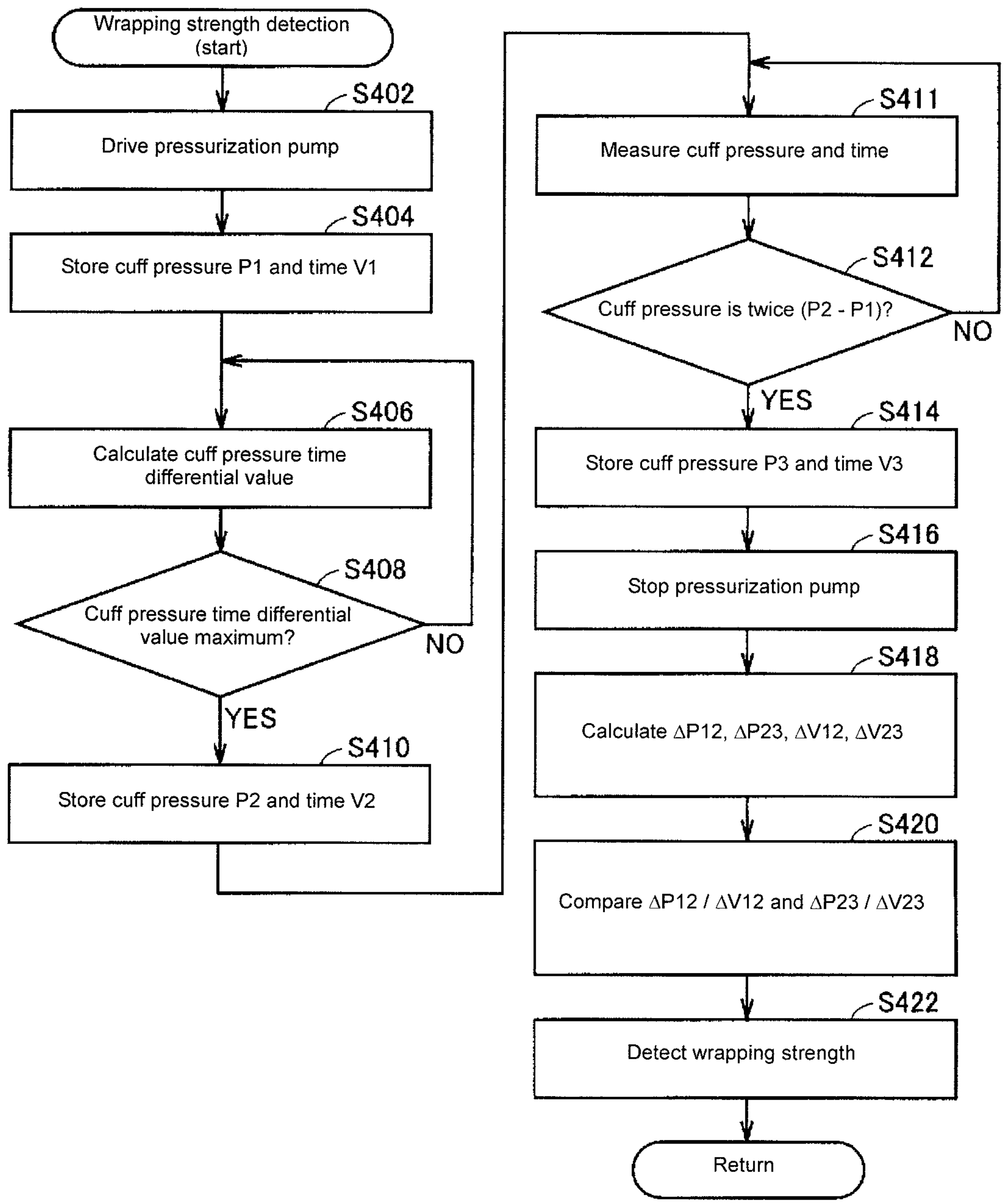
FIG. 6 is a flowchart of a wrapping strength detection process according to the first embodiment.
Figure 7:
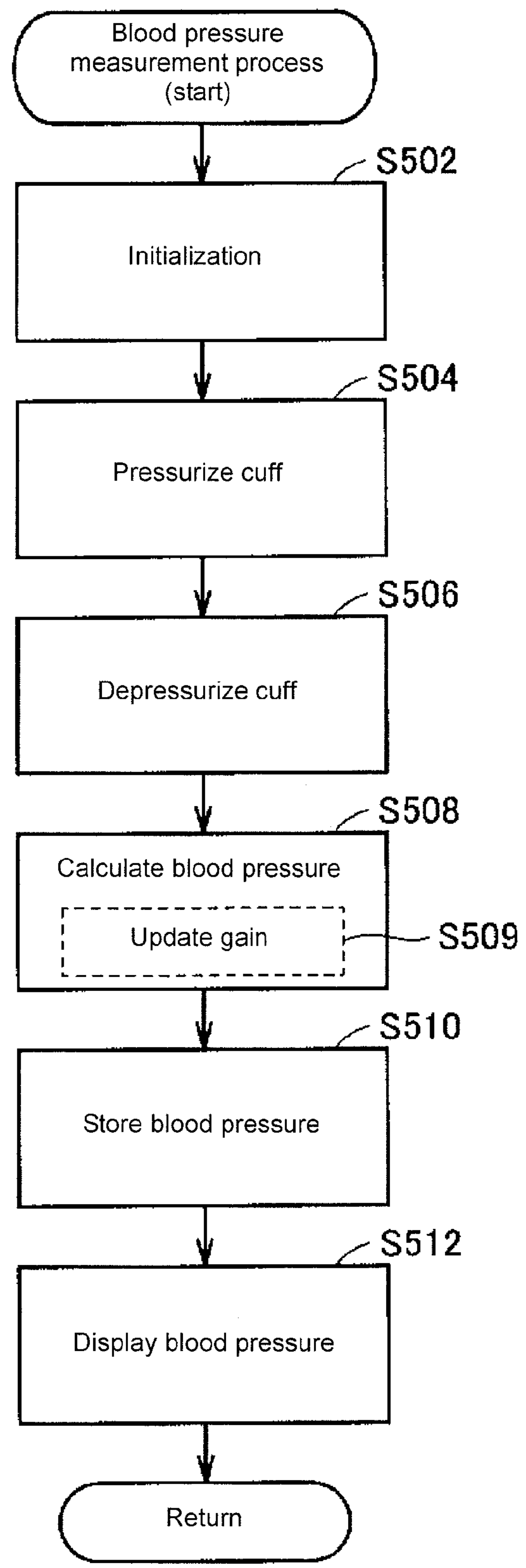
FIG. 7 is a flowchart of a blood pressure measurement process according to the first embodiment.

In the present embodiment, while the blood pressure measurement process is carried out according to the process flowchart of FIGS. 5 to 7, the wrapping strength of the cuff 20 with respect to the measurement site is detected prior to the blood pressure measurement. That is, on the basis of the cuff pressure of the cuff 20 that the person to be measured manually wrapped around the measurement site and the change in volume of the fluid (air in the present embodiment) supplied to the cuff 20, i) fluid volume ΔV12 necessary for the cuff pressure to become from atmospheric pressure P1 to pressure P2, and ii) fluid volume ΔV23 necessary for the cuff pressure to become pressure P2 to pressure P3 are detected, and iii) change rate of the fluid volume ΔV12 and ΔV23 is calculated to thereby detect the wrapping strength of the cuff 20 with respect to the measurement site. The detection result is output and the wrapping strength is presented to the person to be measured to urge rewrapping, so that the subsequent blood pressure measurement can be performed at an appropriate wrapping strength. This will be specifically described.

Here the cuff pressure-volume change relationship obtained in the process of pressurizing the cuff pressure is used, but the cuff pressure-volume change relationship obtained in the process of depressurization may be used.

First, the detection of the cuff pressure-volume change relationship according to an elapse of time from the atmospheric pressure P1 to the pressure P2 and the cuff pressure-volume change relationship according to an elapse of time from the pressure P2 to the pressure P3 will be described.

The pump 33 is driven so that a constant discharging flow rate per unit time is achieved with the cuff 20 wrapped around the measurement site as in FIG. 4 to pressurize the cuff pressure. In this pressurization period, the exhaust valve 34 is closed and the fluid is enclosed in the cuff 20.

In the process of pressurizing or depressurizing the cuff pressure, the timing of elapsed time required for the change of a predetermined cuff pressure (change from pressure P1 to pressure P2 or change from pressure P2 to pressure P3) corresponds to a volume detection unit for detecting the volume of the cuff. The volume detection unit is not limited to timing the elapsed time. That is, assuming the pump 33 is rotationally driven at a constant discharge flow rate (constant rotation number) to calculate the cuff pressure-volume change relationship and the pump 33 discharges fluid of a constant amount by one rotation, the total rotation number (rotation number) of the pump from the start of pressurization may be used in place of the timing of the elapsed time. Furthermore, instead, a parameter (e.g., drive voltage value supplied from pump drive circuit 36 to pump 33) having a known relationship with the pump rotation number may be used, a discharge flow rate itself, or a parameter having a known relationship with the discharge flow rate such as a parameter of the flow rate meter may be used.

Figure 8:
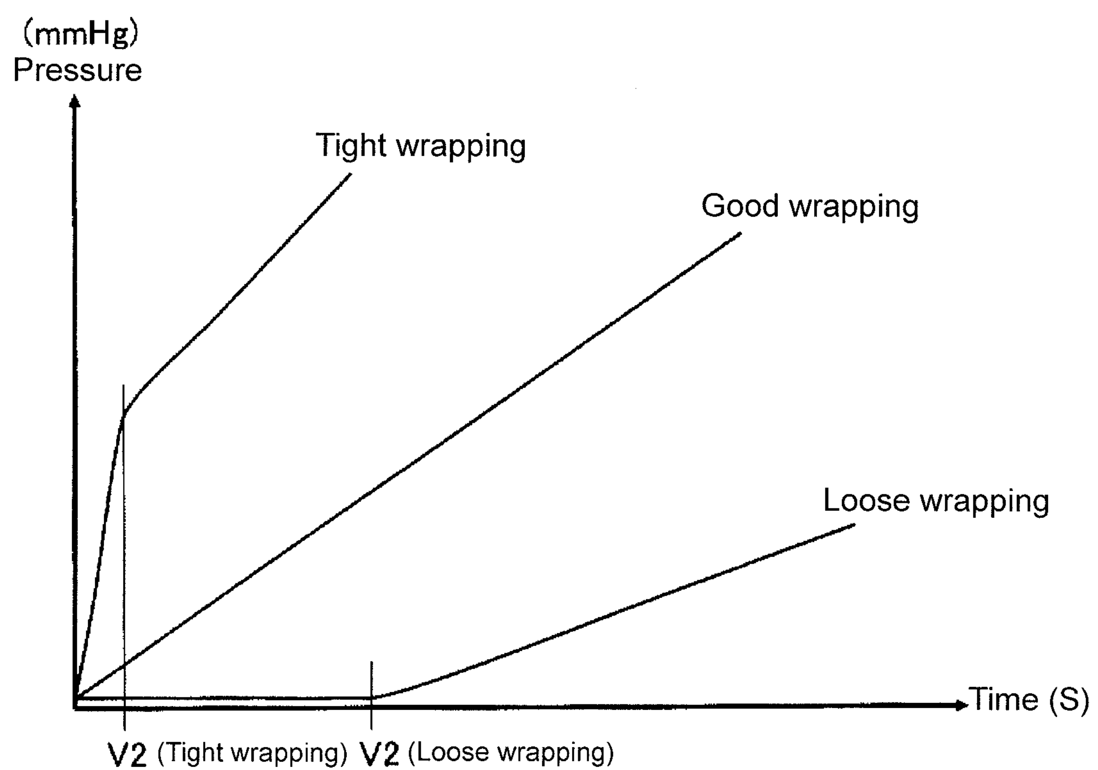
FIG. 8 is a graph showing pressure/pressurization time properties for describing the first embodiment.
Figure 9:
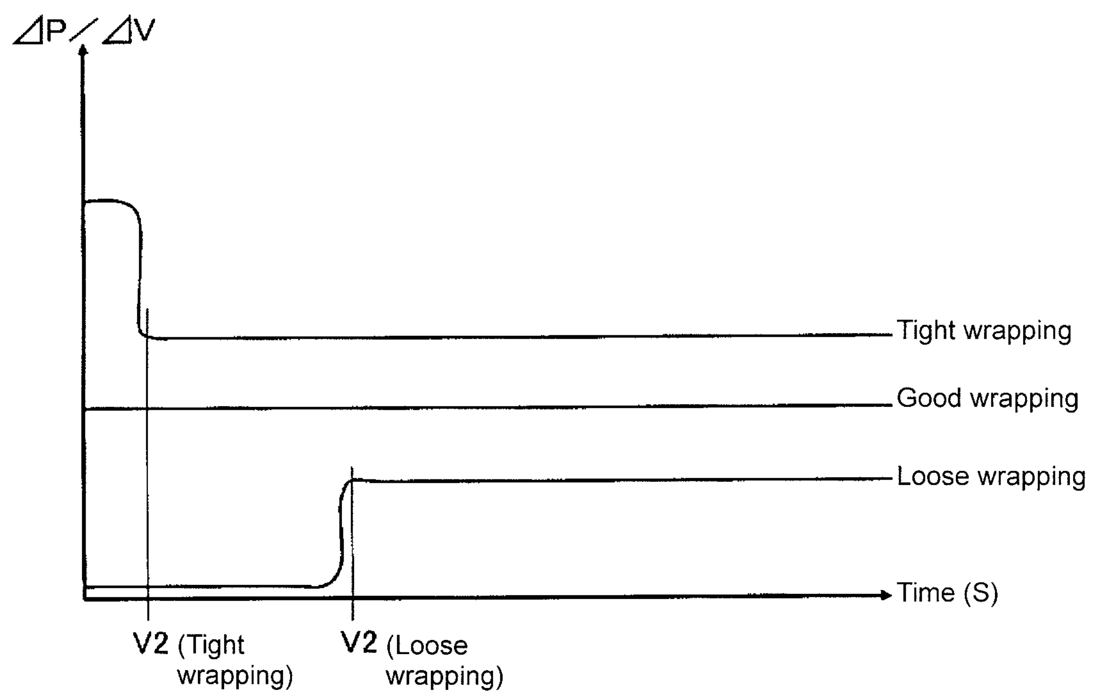
FIG. 9 is a graph of the pressure volume change-pressurization time properties for describing the first embodiment.

With reference to FIGS. 8 and 9 schematically showing the cuff pressure-volume change relationship detected through experiments by the inventors in advance, it can be recognized that the wrapping strength of the cuff 20 on the measurement site has great influence. In FIG. 8, the detected cuff pressure level is shown on the vertical axis, and the pressurization time is shown on the horizontal axis. The cuff pressure-pressurization time properties are thereby shown. In the case of "good" wrapping, the cuff pressure increases with a constant slope from the start of pressurization. In the case of "tight" wrapping, the cuff pressure rapidly rises after the start of pressurization and thereafter rises with a constant slope. In the case of "loose" wrapping, the time until the cuff pressure starts to rise after the start of pressurization becomes long, and rises with a constant slope after the starting to rise. From each graph in FIG. 8, when the cuff pressure becomes a predetermined level, it continues to increase thereafter at a substantially constant pressurization speed based only on the volume of the cuff 20 (air bladder 21) irrespective of the wrapping strength.

In association with the relationship of FIG. 8, FIG. 9 shows a graph of the pressurization time properties of pressure volume change ΔP/ΔV corresponding to the wrapping strength. The pressure volume change ΔP/ΔV is shown on the vertical axis, and the pressurization time is shown on the horizontal axis. According to the relationship of FIG. 8, a constant pressure volume change ΔP/ΔV based only on the volume of the cuff 20 (air bladder 21) is obtained regardless of the pressurization time for the case of "good" wrapping. In the case of "tight" wrapping, the value of the pressure volume change ΔP/ΔV is constant immediately after the start of pressurization but thereafter rapidly becomes smaller, and then maintains constant. In the case of "loose" wrapping, the value of the pressure volume change ΔP/ΔV barely changes for a certain time from after the start of pressurization, but increases at once at a certain time point and maintains a substantially constant value thereafter.

Figure 10:
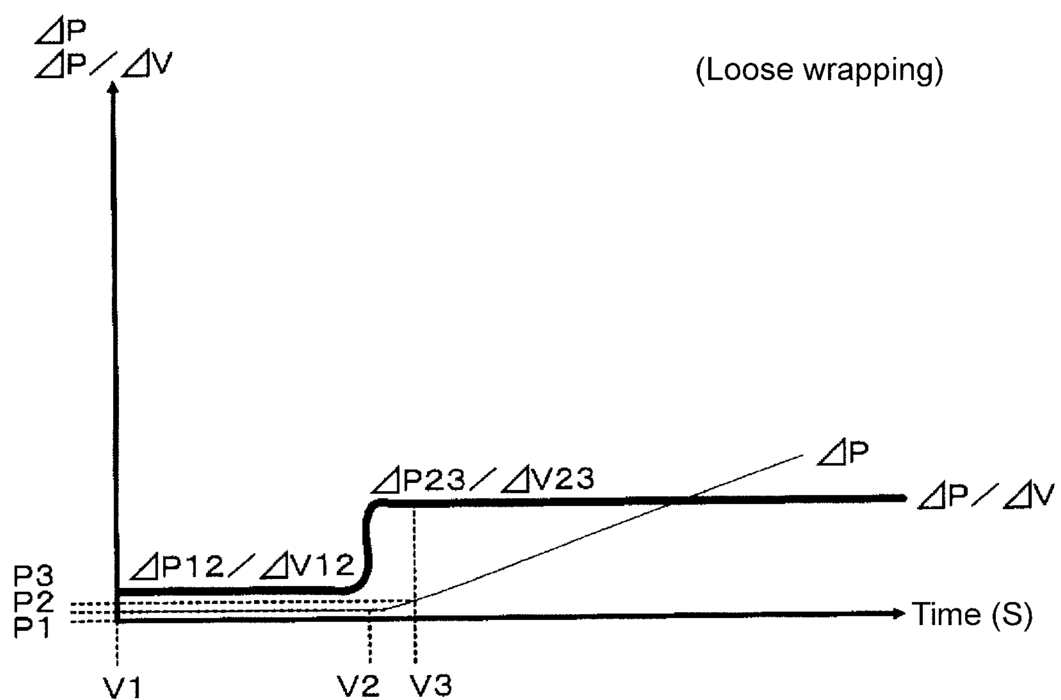
FIG. 10 is a graph of the pressure volume change-pressurization time properties ("loose" wrapping) for describing the first embodiment.

Therefore, the wrapping strength of the cuff 20 to the measurement site and the circumferential length of the measurement site can be detected by using the properties described in FIGS. 8 and 9. Specifically, the wrapping strength is detected according to a flowchart of FIG. 6 to be described later. Upon describing such detection, the properties (pressure volume change (ΔP/ΔV) property) corresponding to the wrapping strength of FIGS. 10 to 12 will be referenced.

(Flowchart of Measurement Process)

FIG. 5 shows an overall process flowchart for the blood pressure measurement according to the present embodiment. The processes complying with the flowchart are stored in a predetermined storage region of the memory 39 as a program in advance, where the measurement process of FIG. 5 is realized when the CPU 100 reads out the program from the memory 39 and executes the same.

In measurement, the person to be measured is assumed to manually wrap the cuff 20 around the measurement site in advance, as shown in FIG. 4.

When the person to be measured operates the switch 41C to instruct the start of measurement, an initialization process is carried out (step S202). The air in the air bladder 21 of the cuff 20 is then exhausted, and the cuff pressure becomes substantially equal to the atmospheric pressure.

The wrapping strength detection process is then carried out by the wrapping strength/circumferential length detection unit 130 (step S204). The details of this process will be described later. After the wrapping strength detection process is finished, the detection result of the wrapping strength is temporarily stored in a predetermined region of the memory 39 through the memory access unit 150 (step S206). The temporarily stored detection result of the wrapping strength is stored in the measurement data MDi as data WND in association with the blood pressure measurement result, to be described later.

Figure 16:
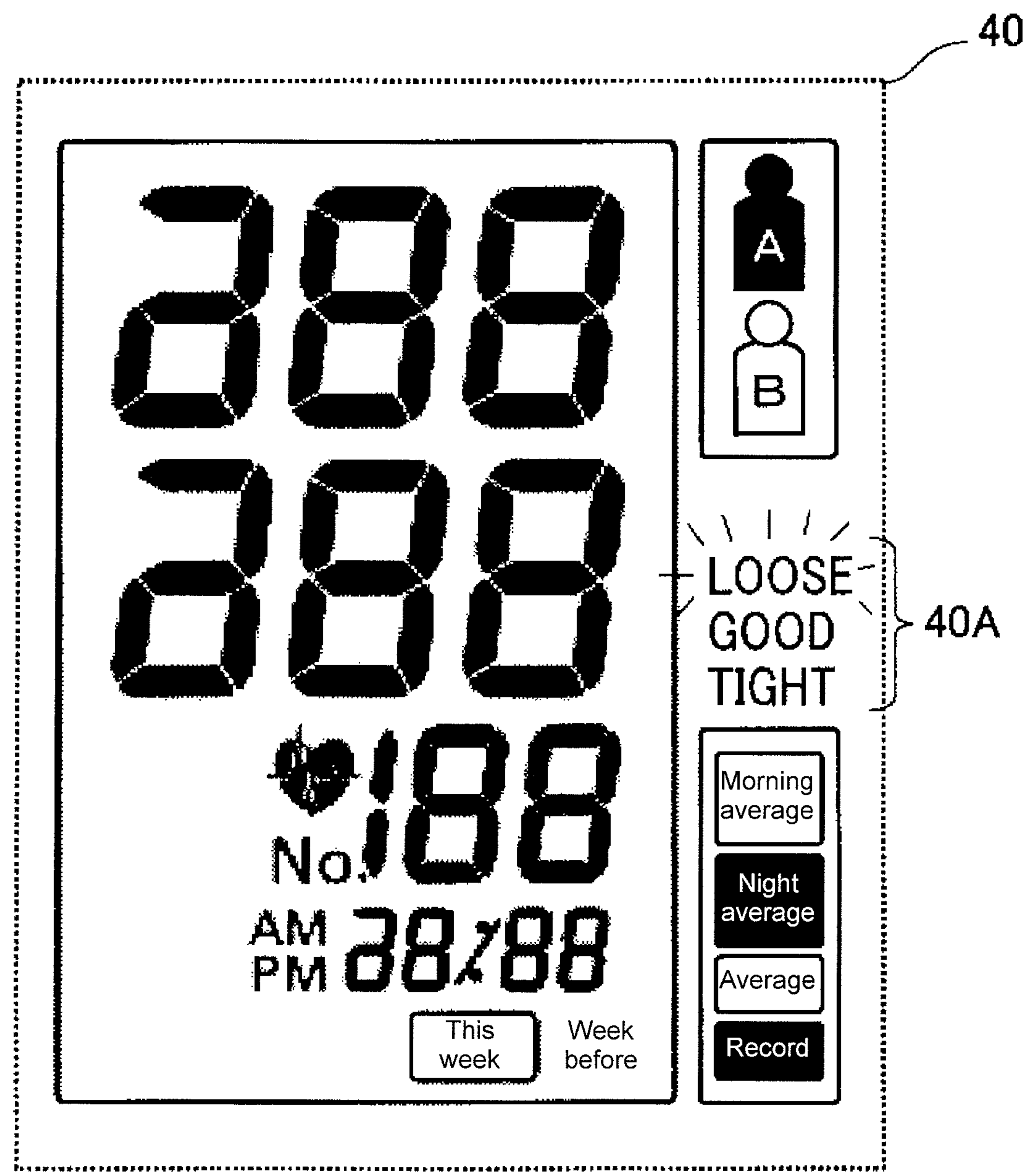
FIG. 16 is a view describing one example of a wrapping strength display according to the first embodiment.

The detection result of the wrapping strength is displayed on the display unit 40 through the display control unit 160 (step S208). One example of such display is shown in FIG. 16. In FIG. 16, the wrapping strength is displayed in the data 40A of the screen of the display unit 40. In FIG. 16, the detected wrapping strength is "loose", and hence, the flashing character "LOOSE" is displayed. The user who recognizes the display rewraps the cuff 20 with respect to the measurement site so as to be tight if "loose" is recognized and to be loose if "tight" is recognized. The user does not redo the wrapping if "good" is recognized.

When the CPU 100 detects that "loose" (LOOSE) or "tight" (TIGHT) is detected according to the detection result of the wrapping strength (NO in step S210), all the air in the air bladder 21 of the cuff 20 is exhausted (step S215). The blood pressure measurement is then cancelled (forcibly terminated). The user then can smoothly redo the wrapping.

The user again operates the switch 41C of the operation unit 41 if the wrapping is done over. The CPU 100 determines whether or not the switch 41C is operated by the user (step S216).

If determined that the switch 41C is operated (YES in step S216), the process returns to step S204 and the wrapping strength detection process (step S204) is similarly carried out to start the blood pressure measurement. If not determined that the switch 41C is operated (NO in step S216), the blood pressure measurement is not carried out, and a series of processes is terminated.

When determining that the wrapping strength of the cuff 20 with respect to the measurement site is "good" (GOOD) wrapping (YES in step S210) according to the detection result of the wrapping strength, the CPU 100 proceeds to a circumferential length detection process (step S212), display of detection result (step S213), and blood pressure measurement process (step S214). After the blood pressure measurement is completed in the blood pressure measurement process, the series of processes is terminated.

(Wrapping Strength Detection Process)

With reference to FIG. 6, the wrapping strength/circumferential length detection unit 130 controls the pump drive circuit 36 for pressurization to drive the pump 33 with a constant discharge flow rate through the pressure adjustment unit 110 (step S402). In this case, the cuff pressure signal detected by the pressure detection unit 101 based on the signal input through the oscillation circuit 35 as well as the timing data input from the timing unit 43 are input, and start to be stored as pressure change data 392 in the storage region E2 in association with the time instructed by the cuff pressure and timing data. The starting pressure that is the cuff pressure detected at the start of pressurization is stored as pressure P1 and the pressurization start time is stored as time V1 (step S404).

The pressure change data 392 indicates waveform data showing the change over time of the cuff pressure according to the elapse of time after the start of pressurization. The differential calculating portion 131 calculates the cuff pressure differential value by differentiating the waveform data indicated by the pressure change data 392 based on time every time the cuff pressure is detected.

The calculated cuff pressure differential value is provided to the differential maximum value detecting portion 133. The differential maximum value detecting portion 133 compares with the cuff pressure differential value input immediately before every time the cuff pressure differential value is input. The calculation of the cuff pressure differential value and the comparison with the previous calculation value are repeated until the maximum value of the cuff pressure differential value is detected (steps S406, S408).

With the cuff pressure when the cuff pressure differential value is detected as maximum as pressure P2 and the time thereof as time V2, they are stored in the storage region E4 in association with each other (step S410).

As shown in FIGS. 8 and 9, the time V2 refers to the time the pressurization starts at a substantially constant pressurization speed based only on the volume of the fluid of the cuff 20 (air bladder 21) irrespective of the wrapping strength.

Thereafter, the pressurization is further continued, and the cuff pressure is detected and stored in the storage region E3 in association with time (step S411). The pressurization (step S411) is repeated until the cuff pressure determining portion 135 determines that the detected cuff pressure indicates a pressure of twice the pressure P2 read from the storage region E4 (YES in step S412). Twice is merely an example, and is not limited thereto.

With the cuff pressure of when becoming twice the pressure P2 as pressure P3, and the time thereof as time V3, they are stored in the storage region E4 in association with each other (step S414).

The wrapping strength/circumferential length detection unit 130 then controls the pump drive circuit 36 to stop the pump 33 through the pressure adjustment unit 110 (step S416).

The relationship detecting portion 137 reads out the data stored in the memory 39, and calculates the change ΔP12 that is the difference from the pressure P1 to the pressure P2 and the time required for the cuff pressure to change by ΔP12, that is, the time ΔV12 indicating the time V2−V1 based on the read data. Similarly, the change ΔP23 that is the difference from the pressure P2 to the pressure P3 and the time required for the cuff pressure to change by ΔP23, that is, the time ΔV23 indicating the time V3−V2 are calculated based on the read data (step S418).

The following processes are then carried out by the change amount comparing portion 139. That is, because the discharge flow rate of the pump 33 is constant, the time ΔV12 required to change by the change ΔP12 is proportional to the change of the fluid volume of the cuff of when changed from the cuff pressure P1 to P2. Similarly, the time ΔV23 required to change by the change ΔP23 is proportional to the change of the fluid volume of the cuff of when changed from the cuff pressure P2 to P3. To detect the wrapping strength based on such relationship, the pressure volume change indices ΔP12/ΔV12 and ΔP23/ΔV23 are calculated, and the calculated values thereof are compared (step S420).

The wrapping strength/circumferential length detection unit 130 detects the wrapping strength based on such comparison result, and outputs the detection result. Specifically, if the comparison result is (ΔP12/ΔV12)<(ΔP23/ΔV23), this matches the characteristics of "loose" wrapping of FIG. 8 and FIG. 9, and hence, the wrapping strength of the cuff 20 is detected as "'loose' wrapping" (see FIG. 10).

Figure 11:
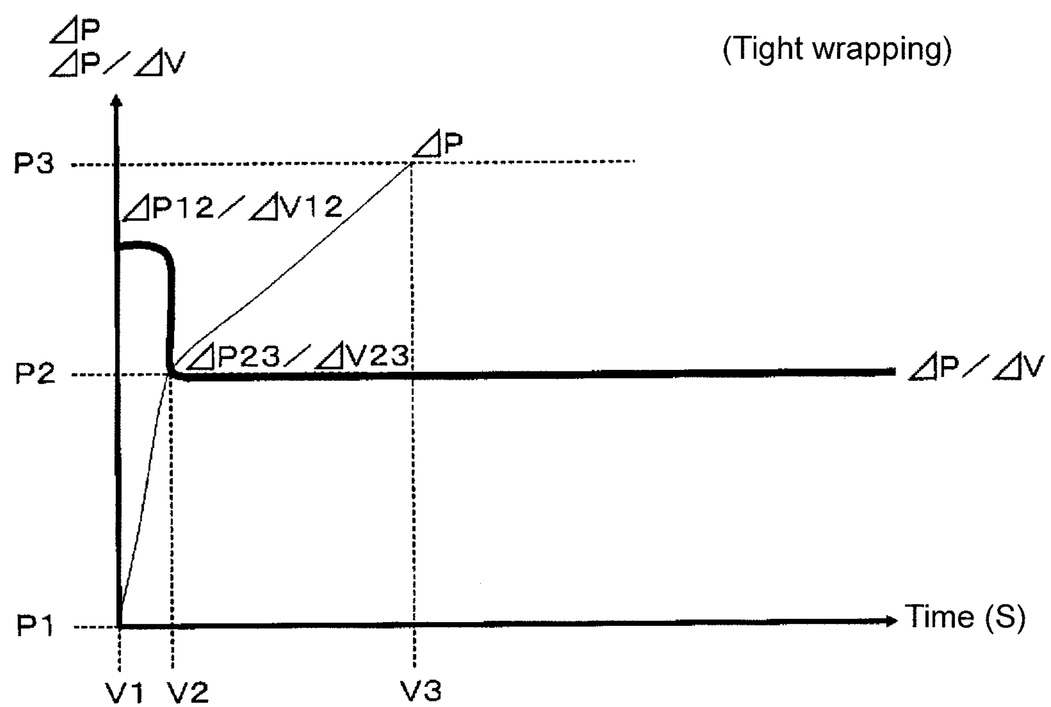
FIG. 11 is a graph of the pressure volume change-pressurization time properties ("tight" wrapping) for describing the first embodiment.

If the comparison result is (ΔP12/ΔV12)>(ΔP23/ΔV23), this matches the characteristics of "tight" wrapping of FIG. 8 and FIG. 9, and hence, the wrapping strength of the cuff 20 is detected as "tight wrapping" (see FIG. 11).

Figure 12:
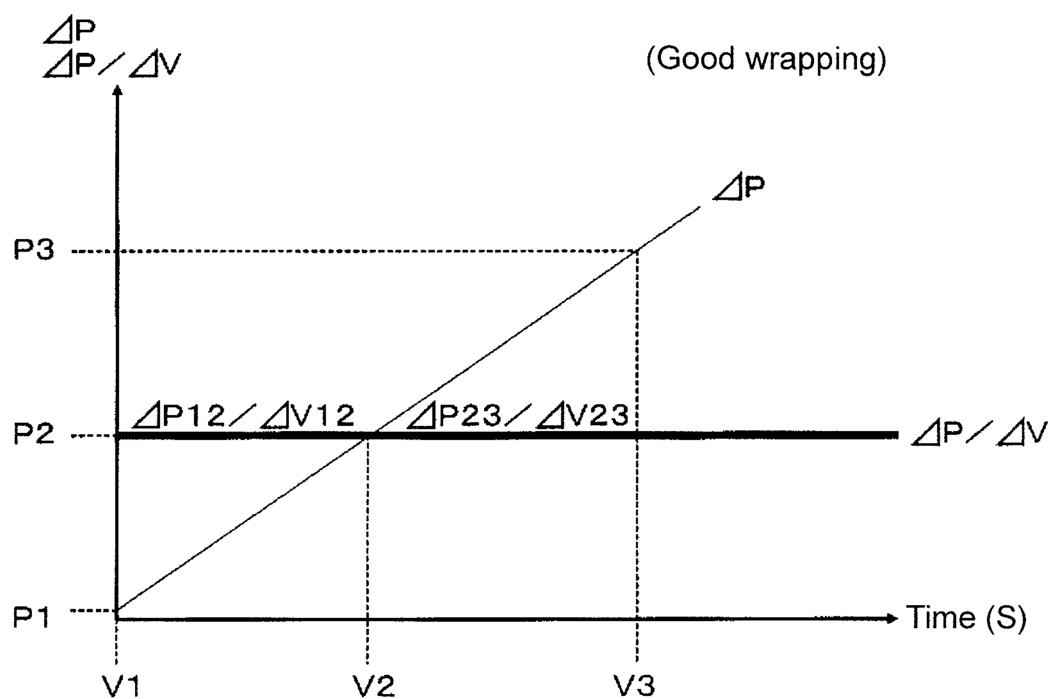
FIG. 12 is a graph of the pressure volume change-pressurization time properties ("good" wrapping) for describing the first embodiment.

If the comparison result is (ΔP12/ΔV12)=(ΔP23/ΔV23), this matches the characteristics of "good" wrapping of FIG. 8 and FIG. 9, and hence, the wrapping strength of the cuff 20 is detected as "good wrapping" (see FIG. 12).

(Detection of Circumferential Length)

The circumferential length (arm circumferential length) of the measurement site may be detected according to the value of ΔP23/ΔV23 by the wrapping strength/circumferential length detection unit 130 after detecting the wrapping strength of the cuff 20 (step S212).

Figure 13:
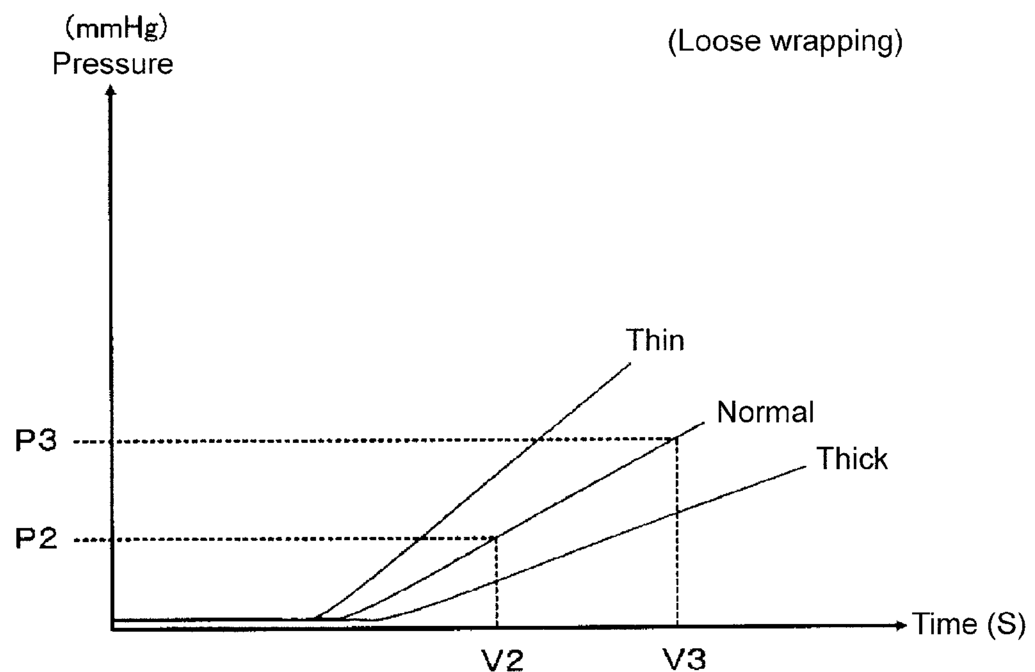
FIG. 13 is a graph of the pressure-pressurization time characteristics (case of loose wrapping) for describing the first embodiment.
Figure 14:
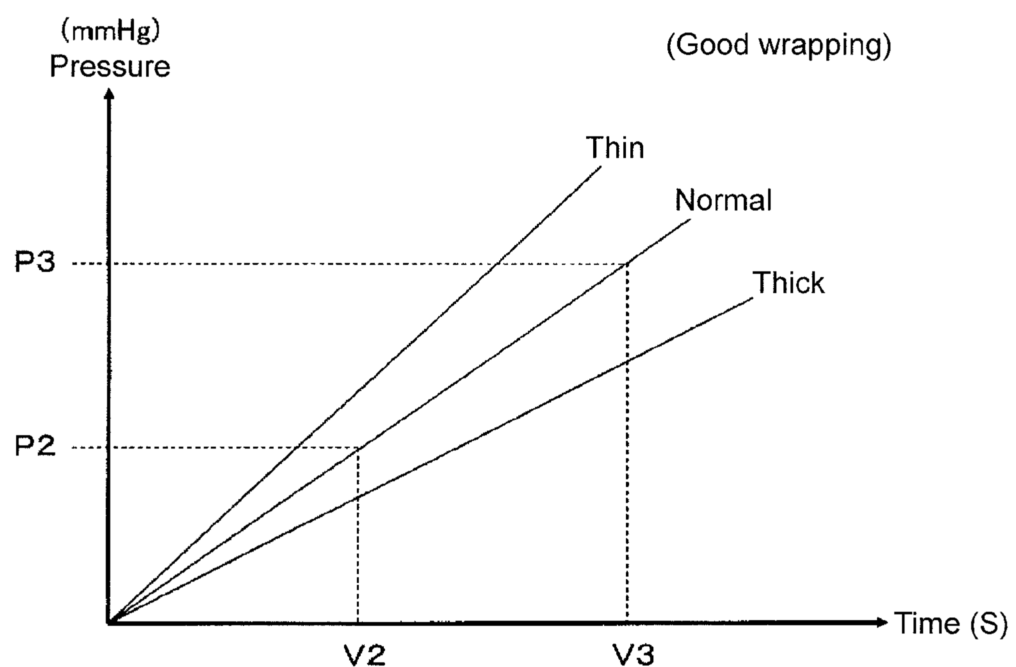
FIG. 14 is a graph of the pressure-pressurization time characteristics (case of good wrapping) for describing the first embodiment.
Figure 15:
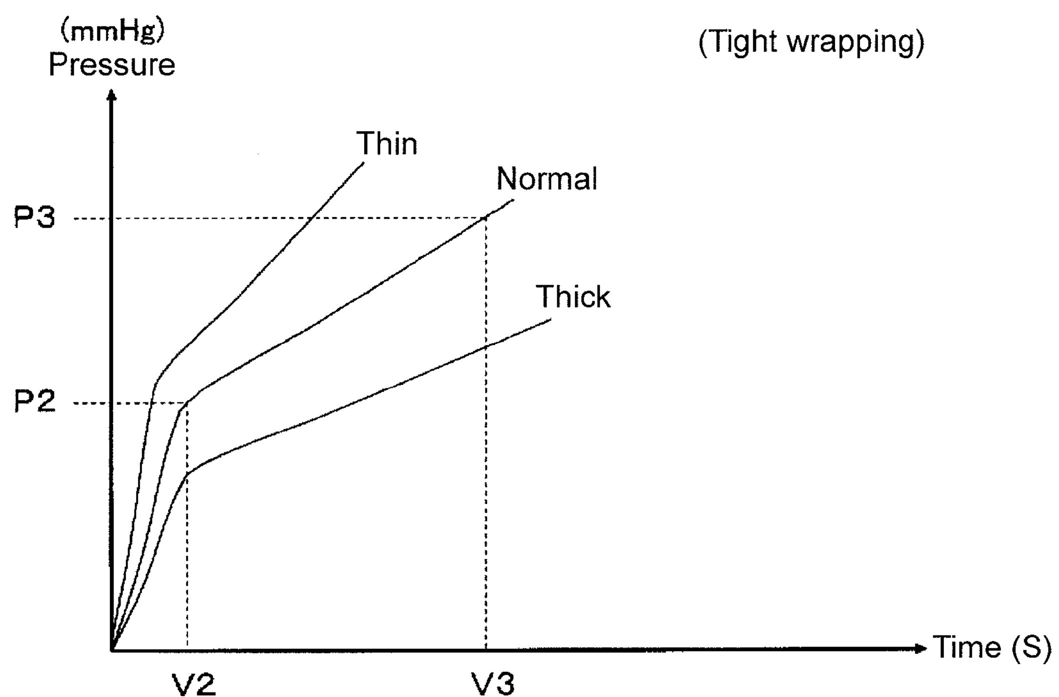
FIG. 15 is a graph of the pressure-pressurization time characteristics (case of tight wrapping) for describing the first embodiment.

FIG. 13 to FIG. 15 show characteristics detected based on data sampled from a great number of subjects using the blood pressure measurement device 1 by the inventors. Specifically, the cuff pressure and the pressurization time characteristics are schematically shown by being sectionalized for every circumferential length (thin arm, normal arm, thick arm) of the measurement site for each of "loose" wrapping, "good" wrapping, and "tight" wrapping.

As described above, in the cuff pressure-volume change relationship of the cuff 20, ΔP23/ΔV23 depends on the volume of the wrapped cuff 20. For instance, if the cuff 20 is wrapped around the measurement site of different circumferential length at the wrapping strength of the same extent, the greater ΔP23/ΔV23 becomes, the shorter the circumferential length (thin arm), and the smaller ΔP23/ΔV23 becomes, the longer the circumferential length (thick arm), as shown in FIG. 13 to FIG. 15.

At the time of measurement, the wrapping strength/circumferential length detection unit 130 searches the table 393 of the memory 39 based on the value of the calculated ΔP23/ΔV23. The data 39D corresponding to the data 39C indicating the value of ΔP23/ΔV23 is read out from the table 393 by the search (step S212). The circumferential length of the measurement site can be detected in such manner.

The detected circumferential length may be output to the blood pressure calculation unit 120 and referenced at the time of blood pressure measurement to enhance the blood pressure measurement accuracy.

The detected circumferential length may be displayed to the outside through the display unit 40 (step S213).

(Blood Pressure Measurement Process)

FIG. 7 is a flowchart showing the blood pressure measurement process executed in step S214 of FIG. 5. The blood pressure measurement process described below is an example, and the method of measuring the blood pressure is not particularly limited.

With reference to FIG. 7, the blood pressure calculation unit 120 first performs an initialization process (step S502). Specifically, the pressure adjustment unit 110 is controlled to exhaust the air of the air bladder 21, correct the pressure sensor 32, and the like.

When in the measurable state, the blood pressure calculation unit 120 controls the pressure adjustment unit 110 to start the drive of the pump 33, and gradually raises the pressure of the air bladder 21 (step S504). After the cuff pressure reaches a predetermined level for blood pressure measurement, the blood pressure calculation unit 120 controls the pressure adjustment unit 110 to stop the pump 33, and gradually opens the exhaust valve 34 that was closed to gradually exhaust the air of the air bladder 21. The cuff pressure is then gradually depressurized (step S506).

The blood pressure calculation unit 120 calculates the blood pressure (maximum blood pressure, minimum blood pressure) according to the procedure complying with the oscillometric method described above (step S508). The pulse rate per predetermined time is also calculated based on the detected pulse wave amplitude information. The method conventionally known may be applied to the calculation of the blood pressure according to the oscillometric method and the calculation of the pulse rate.

After the process of step S508 is finished, the blood pressure calculation unit 120 records the calculated blood pressure and pulse rate according to the format of the record MDi in the storage region E1 of the measurement result of the memory 39 (step S510). The display control unit 160 displays the calculated blood pressure on the display unit 40 (step S512). The series of blood pressure measurement processes are then terminated.

In the process of FIG. 7, the blood pressure is measured in the depressurization process, but measurement can be similarly carried out in the pressurization process.

(Other Measurement Examples)

The blood pressure measurement process described above is assumed to be started when the person to be measured checks the detection result displayed in step S208 and rewraps the cuff 20, and when detected as "good" wrapping in step S210, but the blood pressure measurement process can be carried out even if rewrapping of the cuff 20 by the person to be measured according to the detection result of the wrapping strength is not carried out. In this case, a signal to be used in the blood pressure measurement calculation process is corrected based on the wrapping strength detected in advance in step S204 in the blood pressure calculation of step S508 in the blood pressure measurement process (step S509). The blood pressure measurement accuracy thus can be maintained regardless of the wrapping strength.

The correction will be described. If the wrapping strength is "loose wrapping", the amplitude of the volume pulse wave component contained in the cuff pressure change detected for blood pressure measurement is known to be smaller compared to the normal wrapping strength. The amplitude of the volume pulse wave component is indicated by the pulse wave amplitude information. When the amplitude of the volume pulse wave component becomes small, the determination accuracy of the blood pressure for the blood pressure measurement process lowers. Thus, if detected as "loose wrapping", the gain updating portion 121 searches the table 391 of the storage region E3 of the memory 39, reads the data 39B of the gain corresponding to the data 39A indicating the detected wrapping strength, and updates to increase the gain of the amplifier incorporated in the HPF portion of the pressure detection unit 101 based on the read data 39B. The amplitude of the volume pulse wave component thus can be increased by the relevant amplifier. As a result, the pulse wave amplitude information capable of accurately determining the blood pressure can be detected, and lowering of the blood pressure measurement accuracy can be prevented.

According to the present embodiment, the person to be measured can be urged to wrap the cuff 20 at an appropriate strength because the wrapping strength of the cuff 20 to be wrapped around the measurement site is detected and such detection result is output. The insecurity of the person to be measured on the wrapping strength is thereby resolved, and an accurate blood pressure measurement can be carried out.

Second Embodiment

Figure 17:
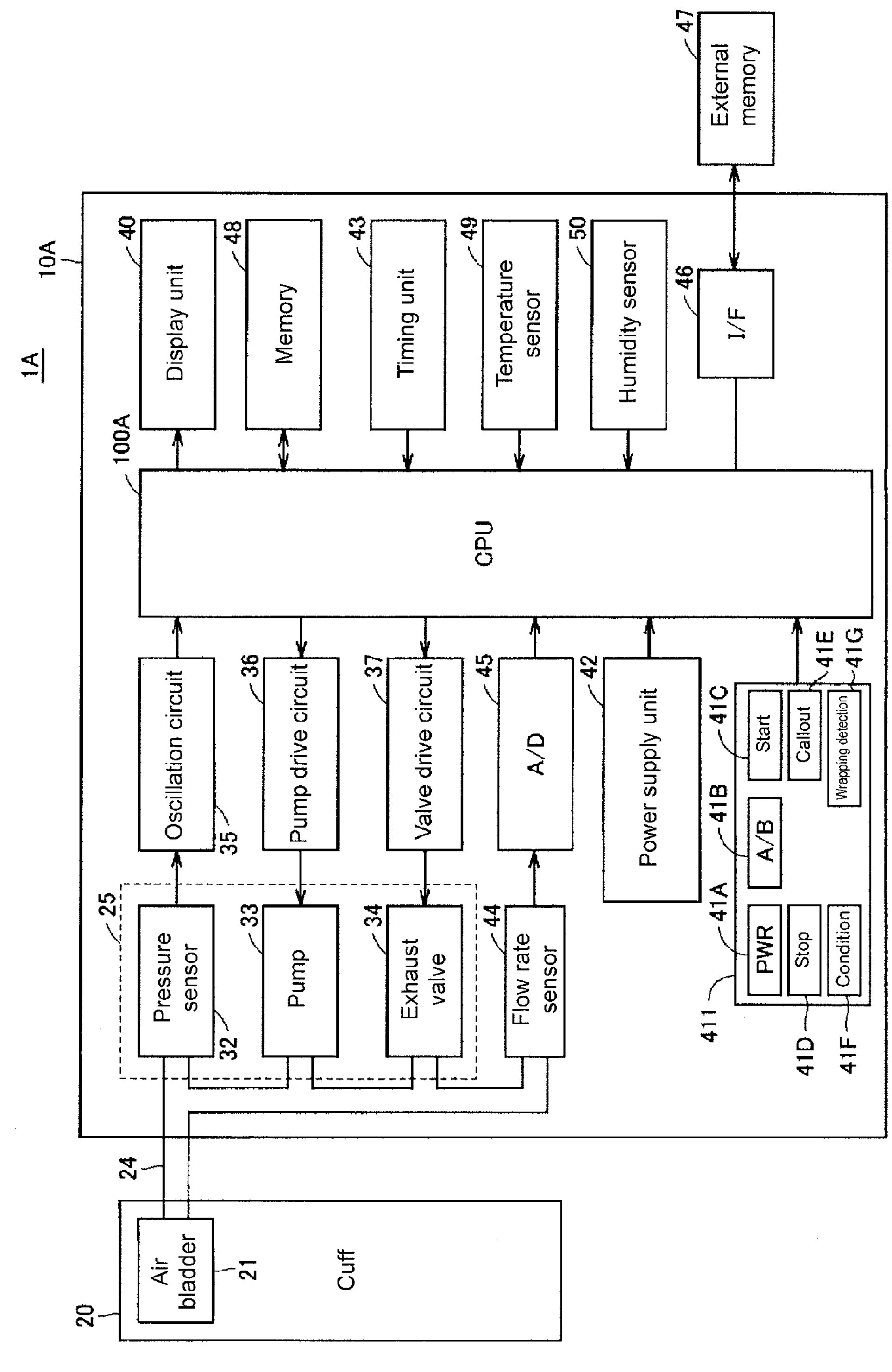
FIG. 17 is a hardware configuration diagram of a blood pressure measurement device according to a second embodiment.

FIG. 17 shows a hardware configuration of a blood pressure measurement device 1A according to a second embodiment. The configuration of the blood pressure measurement device 1A of FIG. 17 is different compared to the configuration of the blood pressure measurement device 1 shown in FIG. 1 in that a main body 10A is arranged in place of the main body 10 of FIG. 1.

Comparing the main body 10 of FIG. 1 and the main body 10A of FIG. 17, the difference lies in that a CPU (Central Processing Unit) 100A, a memory 48, and an operation unit 411 are arranged in place of the CPU 100, the memory 39, and the operation unit 41 of the main body 10. In addition to the configuration of the main body 10, the main body 10A also includes a flow rate sensor 44, an ND (Analog/Digital) conversion circuit 45, an I/F (abbreviation for interface) 46, and a temperature sensor 49 as well as a humidity sensor 50 for detecting temperature and humidity around the blood pressure measurement device 1A.

Similar to the operation unit 41, the operation unit 411 includes the switches 41A to 41E, the switch 41F operated by the person to be measured to input measurement conditions to be described later, and the switch 41G operated by the person to be measured to instruct the start of detection of the wrapping strength of the cuff 20.

The flow rate sensor 44 is connected to the air tube 24 for connecting the main body 10A and the cuff 20 to detect the amount of air, that is, the fluid amount supplied from the pump 33 to the air bladder 21 through the air tube 24 or exhausted from the air bladder 21. The detection signal of the flow rate sensor 44 is provided to the ND conversion circuit 45. The ND conversion circuit 45 inputs the detection signal, converts the input analog detection signal to digital data, and outputs the digital data to the CPU 100A.

The flow rate sensor 44 detects the flow rate flowing in a direction of the air bladder 21 through the connected air tube 24. The electromagnetic method using the "Faraday's law of induction" for the measurement theorem, for example, is applied for the detection method. When a conductive object (air) moves through the magnetic field, an electromotive force generates in the object, and such generated electromotive force is output to the ND conversion circuit 45 through the electrode. The ND conversion circuit 45 converts the analog electromotive force signal to the digital data, and outputs the same to the CPU 100A. The detection method is not limited thereto, and a method of converting the number of rotations of an impeller generated when the flowing air hits the impeller to the flow rate value may be adopted.

In the present embodiment, the fluid amount is assumed to be detected by the flow rate sensor 44 of the blood pressure measurement device 1A. The detection method is not limited to the method of using the flow rate sensor. For instance, if the fluid amount per unit time flowed into and discharged from the cuff 20 at the time of pressurization and depressurization of the cuff pressure is constant, the elapsed time from the start of pressurization or the start of depressurization may be measured, and the fluid amount may be calculated by the integration of the measured time and the constant fluid amount per unit time.

The fluid amount may be detected from the total power amount in a proportional relationship with the fluid amount flowed into and discharged from the cuff 20 at the time of pressurization and depressurization of the cuff pressure.

In order to measure the total power amount, the relationship of the voltage applied to the actuator (pump 33 and valve 34) used in pressurization and depressurization and the consumed current amount is measured in advance, and the measured voltage-consumed current amount relationship is stored in the memory 48. At the time of the blood pressure measurement, the total power amount consumed by the actuator can be calculated based on the voltage applied to the actuator in pressurization or depressurization of the cuff pressure, the applied time period, and the relationship read from the memory 49.

When using the actuator by a rotation mechanism such as a pump for flowing fluid into the cuff 20 or discharging fluid from the cuff 20, the total number of rotations of the actuator required for the flow-in and the discharge may be adopted.

The flow rate sensor 44 is not necessary in the blood pressure measurement device 1A if the fluid amount is substituted with the elapsed time from the start of pressurization or start of depressurization, total power amount or total rotation number, or the like.

The I/F 46 has a function of accessing the external memory 47 prepared in advance at an exterior of the blood pressure measurement device 1A under the control of the CPU 100A. Other configurations shown in FIG. 17 are similar to the corresponding configurations shown in FIG. 1, and thus, the description will be omitted herein.

(Content of Memory 48)

With reference to FIG. 18, the memory 48 stores data including a recording table 394 for recording data related to the blood pressure measurement, tables 395 and 396 referenced to detect the wrapping strength, and a table 397 referenced to detect the arm circumferential length that is the measurement condition.

The recording table 394 stores data of the blood pressure measurement in units of records. Each record includes data 39E of ID (identification) for uniquely identifying the relevant record, data 39F for identifying the person to be measured (user), data 39G of measurement date and time, data 39H including blood pressure value (maximum blood pressure data SBP and minimum blood pressure data DBP) and pulse rate data PLS, and data 391 indicating the attachment state of the cuff 20 at the measurement site, that is, the wrapping strength, and data 39J of a measurement condition. The value indicated by the data 391 is either "OK" or "NG", where "OK" means that the wrapping strength of the cuff 20 detected when the blood pressure value of the corresponding data 39H is measured as "good" wrapping, and "NG" means that the wrapping strength is not "good" wrapping. The measurement condition indicated by the data 39J indicates the arm circumferential length of the measurement site (upper arm) on which the cuff 20 is wrapped at the time of the blood pressure measurement of the corresponding data 39H. The arm circumferential length is indicated by either "L" or "M". "L" means that the arm circumferential length is relatively long. Here, the relationship M<L is satisfied.

The mode of storing the blood pressure measurement data in the recording table 394 is not limited to the units of records as shown in FIG. 18. The mode merely needs to be such in which the detected data 39E to 39J are recorded in association with each other every time the blood pressure is measured.

In the present embodiment, the wrapping strength indicated by the data 391 indicates either "OK" or "NG", but may be one of "tight", "good", or "loose". A numerical value indicating the wrapping strength may be recorded.

In the table 395, data 39K indicating different arm circumferential length, and data 39L of a threshold value related to the fluid amount for detecting the wrapping strength in correspondence to the data 39K are stored. In the table 396, the data 39K indicating different arm circumferential length, and data 39M of a threshold value related to the cuff pressure for detecting the wrapping strength in correspondence to the data 39K are stored. In the table 397, the data 39N indicating different fluid amount, and data 39P of the arm circumferential length in correspondence to the data 39N are stored. The data of the tables 395, 396, and 397 are acquired in advance through experiments, and then stored.

(Function Configuration)

Figure 19:
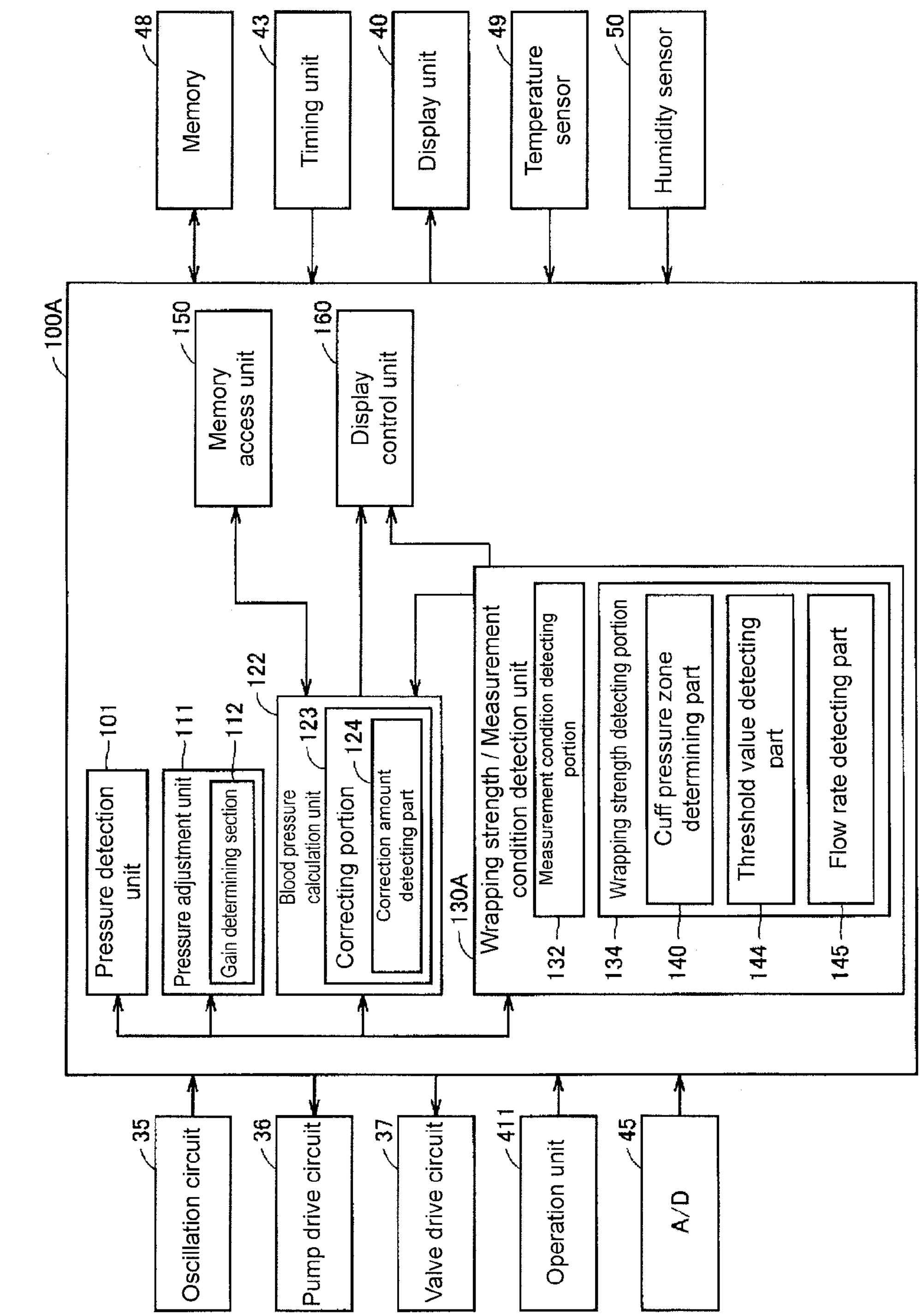
FIG. 19 is a function block diagram of the blood pressure measurement device according to the second embodiment.

In FIG. 19, function blocks of the blood pressure measurement device 1A according to the present embodiment are shown. In FIG. 19, the illustration of hardware that does not directly exchange signals with the CPU 100A is omitted.

With reference to FIG. 19, the CPU 100A includes a pressure detection unit 101, a pressure adjustment unit 111 including a gain determining portion 112, a blood pressure calculation unit 122, a wrapping strength/measurement condition detection unit 130A, a memory access unit 150 for accessing data of the memory 48, and a display control unit 160 for controlling the display of the data by the display unit 40. The pressure detection unit 101 has functions and configurations similar to the first embodiment.

Similar to the pressure adjustment unit 110, the pressure adjustment unit 111 controls the cuff pressure of the cuff 20 by controlling the operation of the pump drive circuit 36 and the valve drive circuit 37. The rotation number of the pump 33 is controlled by the voltage applied from the pump drive circuit 36. The fluid amount per unit time supplied to the air bladder 21 by the pump 33 is variably controlled by controlling the rotation number. The pump drive circuit 36 applies the voltage of a level based on the gain data provided from the gain determining portion 112 to the pump 33. Therefore, the fluid amount supplied per unit time to the air bladder 21 is controlled according to the gain data determined by the gain determining portion 112.

The blood pressure calculation unit 122 performs the calculation of the blood pressure according to the oscillometric method and the calculation of the pulse rate, similar to the blood pressure calculation unit 120 of the first embodiment.

In the present embodiment, the blood pressure calculation unit 122 includes a correcting portion 123 for correcting the calculated blood pressure value. The correcting portion 123 includes a correction amount detecting part 124. The correction amount detecting part 124 detects the data amount (hereinafter referred to as correction amount) to be used in the correction of the blood pressure value based on the provided data. The correcting portion 123 corrects the blood pressure value using the detected correction amount.

The wrapping strength/measurement condition detection unit 130A includes a measurement condition detecting portion 132 for detecting the measurement condition at the time of the blood pressure measurement, and a wrapping strength detecting portion 134 for detecting the wrapping strength of the cuff 20 with respect to the measurement site. The wrapping strength detecting portion 134 includes a cuff pressure zone determining part 140 for determining the cuff pressure for detecting the wrapping strength, a threshold value detecting part 144, and a flow rate detecting part 145 for detecting the fluid amount to be supplied to the air bladder 21. The function of each part of the wrapping strength detecting portion 134 will be described later.

The memory access unit 150 and the display control unit 160 have functions similar to those in the first embodiment.

(Outline of Wrapping Strength Detection)

In the present embodiment, the volume of the air bladder 21 of the cuff 20 is described as the amount of fluid flowing into or discharged from the air bladder 21 at the time of pressurization and depressurization. When referring to the fluid flowing into the air bladder 21 or being discharged from the air bladder 21, it is sometimes referred to as flowing into the cuff 20 or being discharged from the cuff 20.

In the present embodiment, the wrapping strength of the measurement site (upper arm) of the cuff 20 is basically detected based on the change of the cuff pressure and the relationship (cuff pressure-volume change relationship) of the change of the volume of the cuff 20 detected therewith. That is, the cuff pressure-volume change relationship is detected based on the change in the bulging amount of the cuff 20 (=volume of cuff 20) dependent on the wrapping strength. Specifically, if the cuff 20 is wrapped around the upper arm in the "loosely" wrapped state, that is, if the cuff 20 is wrapped around with a space, the cuff pressure does not rise even if the fluid is fed into the cuff 20 until the cuff 20 is brought into contact with the attachment site. On the other hand, if the cuff 20 is wrapped around in the "tightly" wrapped state, the cuff pressure rises by simply feeding a small amount of fluid into the cuff 20. In other words, the bulging amount of the cuff 20 (=volume of cuff 20) changes depending on the wrapping strength of the cuff 20 with respect to the measurement site.

According to the experiments conducted by the inventors, a knowledge that the measurement condition is also a factor that changes the volume of the cuff 20 in addition to the wrapping strength is obtained, and a knowledge that the volume of the cuff 20 with respect to the same cuff pressure changes by the measurement condition even if the same cuff 20 is wrapped around the measurement site at the same strength is obtained. The measurement condition includes arm circumferential length, quality (hard or soft) of the measurement site, size of the cuff 20, temperature or humidity around the blood pressure measurement device 1A at the time of measurement, characteristics of the pump 33 and the valve 34 for pressurization and depressurization, fluid volume remaining in the cuff 20, and the like. The quality of the measurement site is indicated by information of the body composition such as BMI (Body Mass Index) and body fat percentage.

More specifically, with respect to the arm circumferential length, the volume of the cuff 20 with respect to the same cuff pressure becomes greater as the circumferential length of the measurement site becomes longer even if the same cuff 20 is wrapped around the measurement site.

Similarly, with respect to the quality of the measurement site, the volume of the cuff 20 with respect to the same cuff pressure becomes greater as the measurement site becomes softer and not muscular.

Similarly, with respect to the size of the cuff 20, the volume of the cuff 20 with respect to the same cuff pressure becomes greater as the size becomes greater.

With respect to the temperature or the humidity, the air bladder 21 of the cuff 20 tends to easily stretch under the environment of high temperature or high humidity. Thus, the volume of the cuff 20 with respect to the same cuff pressure becomes greater as the temperature or the humidity becomes higher. The temperature is detected by the temperature sensor 49 and the humidity is detected by the humidity sensor 50.

With respect to the characteristics of the pump 33 for pressurization, the time, the total power amount, and the rotation number (=apparent cuff volume) necessary for feeding the same amount of fluid to the cuff 20 with respect to the same cuff pressure differ due to the variation in the characteristics of the pump 33.

With respect to the characteristics of the valve 34 for depressurization, and the time, the total power amount (=apparent cuff volume) necessary for discharging the same amount of fluid from the cuff 20 with respect to the same cuff pressure differ due to the variation in the characteristics of the valve 34.

The fluid volume remaining in the cuff 20 is as follows. The depressurization of the cuff 20 depends on natural exhaust by opening the valve 34, and hence, the fluid sometimes remains in the cuff 20 immediately after the blood pressure measurement is terminated and the cuff pressure is depressurized to 0 mmHg. Thus, when the blood pressure measurement is continuously carried out, the volume of the cuff 20 becomes small on the appearance due to the fluid volume remaining in the cuff 20 after the termination of the previous blood pressure measurement.

Therefore, the wrapping strength of the cuff 20 can be accurately detected by being detected based on the measurement condition and the cuff pressure-volume change relationship compared to being detected from only the cuff pressure-volume change relationship. In the present embodiment, the arm circumferential length is mainly used for the measurement condition to simplify the description, but other types of measurement conditions may be used. Two or more types of measurement conditions may be combined and used.

(Flowchart of Measurement Process)

Figure 20:
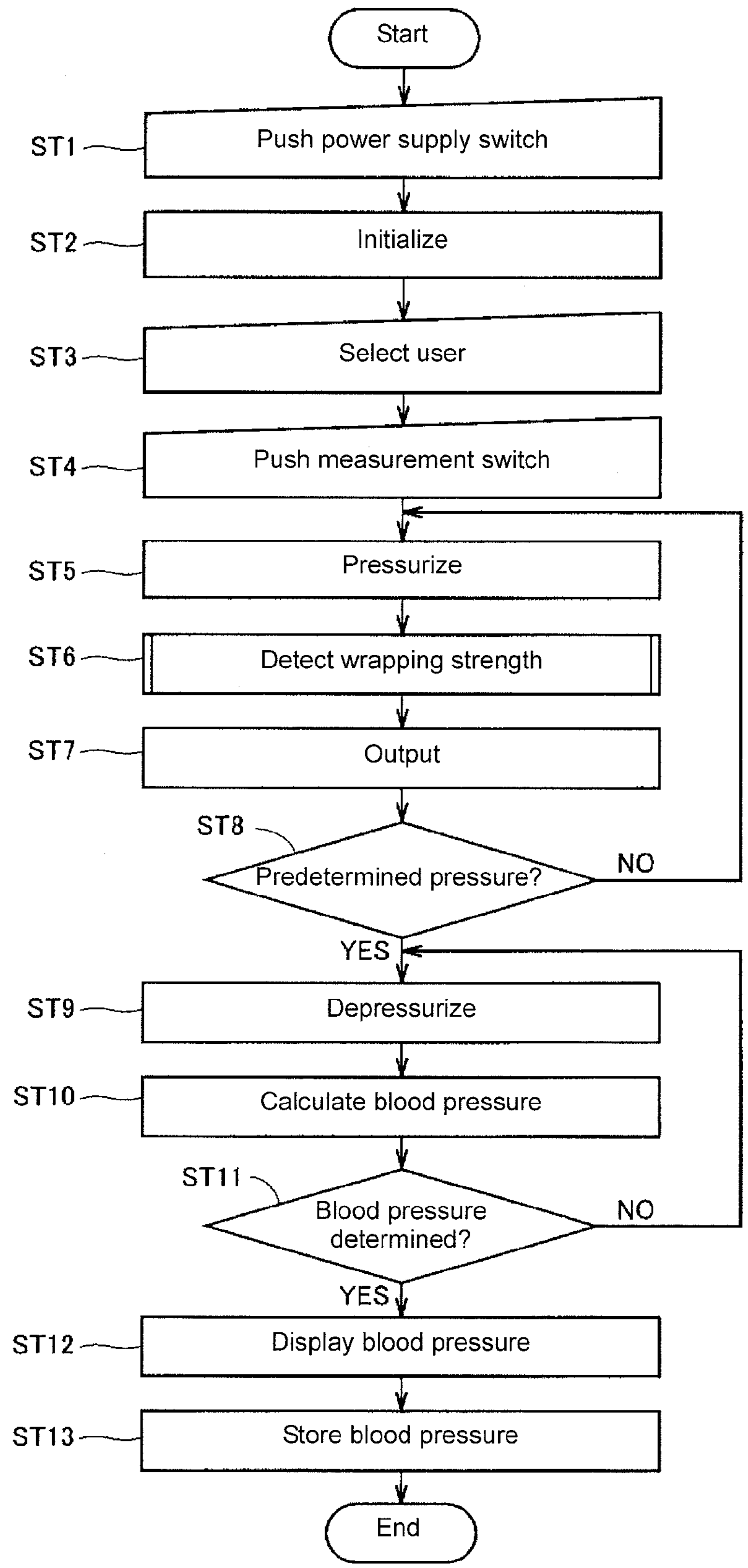
FIG. 20 is an overall process flowchart of the blood pressure measurement according to the second embodiment.

FIG. 20 shows an overall process flowchart for the blood pressure measurement according to the present embodiment. The processes according to the flowchart are stored in a predetermined storage region of the memory 48 as program in advance, where the measurement process of FIG. 20 is realized when the CPU 100A reads out the program from the memory 48 and executes the same.

In measurement, the person to be measured is assumed to manually wrap the cuff 20 around the measurement site in advance, as shown in FIG. 4.

When the power supply switch 41A is operated by the person to be measured (step ST1), the operation unit 411 detects that the power supply switch 41A is operated, and outputs the detection signal to the CPU 100A. The CPU 100A initializes the work region of the memory 48, and carries out the 0 mmHg adjustment of the pressure sensor 25 (step ST2).

When the user selection switch 41B is operated by the person to be measured (step ST3), the operation unit 411 detects that the user selection switch 41B is operated and outputs the detection signal to the CPU 100A. The CPU 100A acquires the identification information of the user selected based on the detection signal.

Thereafter, when the measurement switch 41C is operated by the person to be measured (step ST4), the operation unit 411 detects that the measurement switch 41C is operated and outputs the detection signal to the CPU 100A. The pressure adjustment unit 111 outputs a control signal to the valve drive circuit 37 and outputs a control signal including the gain data to the pump drive circuit 36 according to the input of the detection signal. The valve drive circuit 37 closes the valve 34 based on the provided control signal. The pump drive circuit 36 controls the rotation of the pump 33 based on the provided control signal. The fluid then starts to be supplied to the air bladder 21 and the cuff pressure rises (step ST5). After the pressurization is started, the cuff pressure is detected by the pressure detection unit 101 based on the output signal of the pressure sensor 25. The pressure detection unit 101 compares the detected cuff pressure and the predetermined pressure read out from the memory 48, and determines whether or not the cuff pressure indicates the predetermined pressure based on the comparison result. If determined that the cuff pressure indicates the predetermined pressure by the pressure detection unit 101 (YES in step ST8), the pressurization operation by the pressure adjustment unit 111 is terminated.

In the pressurization process from the start to the end of the pressurization, the wrapping strength of the cuff 20 is detected by the wrapping strength detecting portion 134 (step ST6) while determined that the cuff pressure does not indicate the predetermined pressure (NO in step ST8), and the detection result is displayed on the display unit 40 by the display control unit 160 (step ST7). The information of the wrapping strength is continuously displayed until the blood pressure measurement is terminated. The detection of the wrapping strength of the cuff 20 will be hereinafter described.

After pressurizing the cuff pressure to a predetermined pressure (YES in step ST8), the pressure adjustment unit 111 outputs a control signal to the valve drive circuit 37. The valve drive circuit 37 continues until the calculation of the blood pressure is confirmed (YES in step ST11) so as to gradually open the valve 34 according to the control signal. The cuff pressure is thus gradually depressurized (step ST9). The depressurization is continued while the calculation of the blood pressure is not confirmed (NO in step ST11).

The blood pressure is calculated in the depressurization process. That is, the blood pressure calculation unit 122 calculates the blood pressure value according to the oscillometric method based on the detected volume pulse wave signal, similar to the blood pressure calculation unit 120. The pulse rate is detected through a well known method at the time of calculating the blood pressure (step ST10). When detecting that both the maximum blood pressure and the minimum blood pressure are calculated (YES in step ST11), the valve is completely opened and the air in the cuff 20 is rapidly exhausted.

The calculated blood pressure value is displayed on the display unit 40 (step ST12). A record for storing the data 39F indicating the identification of the user input in step ST3, the data 39G of the measurement date and time based on the timing data of the timing unit 43, the data 39H of the calculated blood pressure value and the pulse rate, and the data 391 of the detected cuff wrapping strength is generated, and the record is recorded in the recording table 394 of the memory 48 (step ST13). When the record is recorded, the data 39E of the ID is additionally stored in the relevant record.

(Concept of Wrapping Strength Detection Process)

Figure 21:
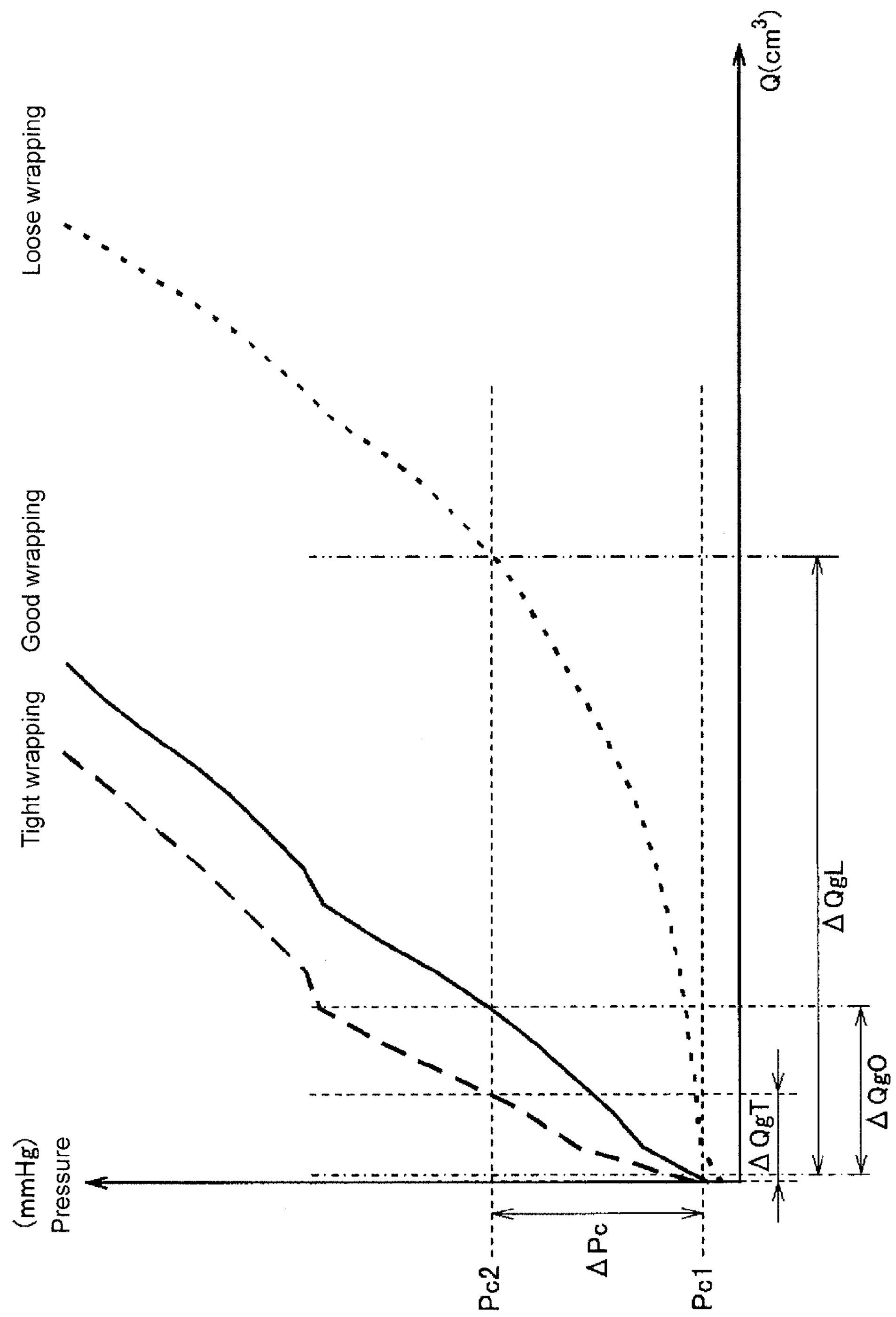
FIG. 21 is a view showing the relationship of the wrapping strength of the cuff and the change in the cuff pressure.

The inventors acquired the relationship between the wrapping strength of the cuff 20 and the change in the cuff pressure of FIG. 21 through experiments. The fluid amount supplied to the cuff 20 to change the cuff pressure is shown on the horizontal axis of the graph of FIG. 21, and the cuff pressure is shown on the vertical axis. As shown in the figure, the fluid amount Q required for the cuff pressure to change by the value range ΔPc (indicates the continuing value range from Pc1 to Pc2 of the cuff pressure in FIG. 21) differs according to the wrapping strength ("tight" wrapping, "good" wrapping, and "loose" wrapping) of the cuff 20. That is, in FIG. 21, the required fluid amount is ΔQgT in the case of the "tight" wrapping, QgO in the case of "good" wrapping, and QgL in the case of "loose" wrapping. Therefore, the fluid to be supplied to the cuff 20 for the cuff pressure to change by ΔPc can be detected, and the wrapping strength of the cuff 20 can be detected based on the detected fluid amount and a predetermined threshold value.

The change in fluid amount shown in FIG. 21 corresponds to the change in volume of the cuff 20 (air bladder 21). As described above, the wrapping strength is detected based on the cuff pressure-volume change relationship (see FIG. 21) regarding the cuff 20 and the measurement condition (arm circumferential length).

Figure 22:
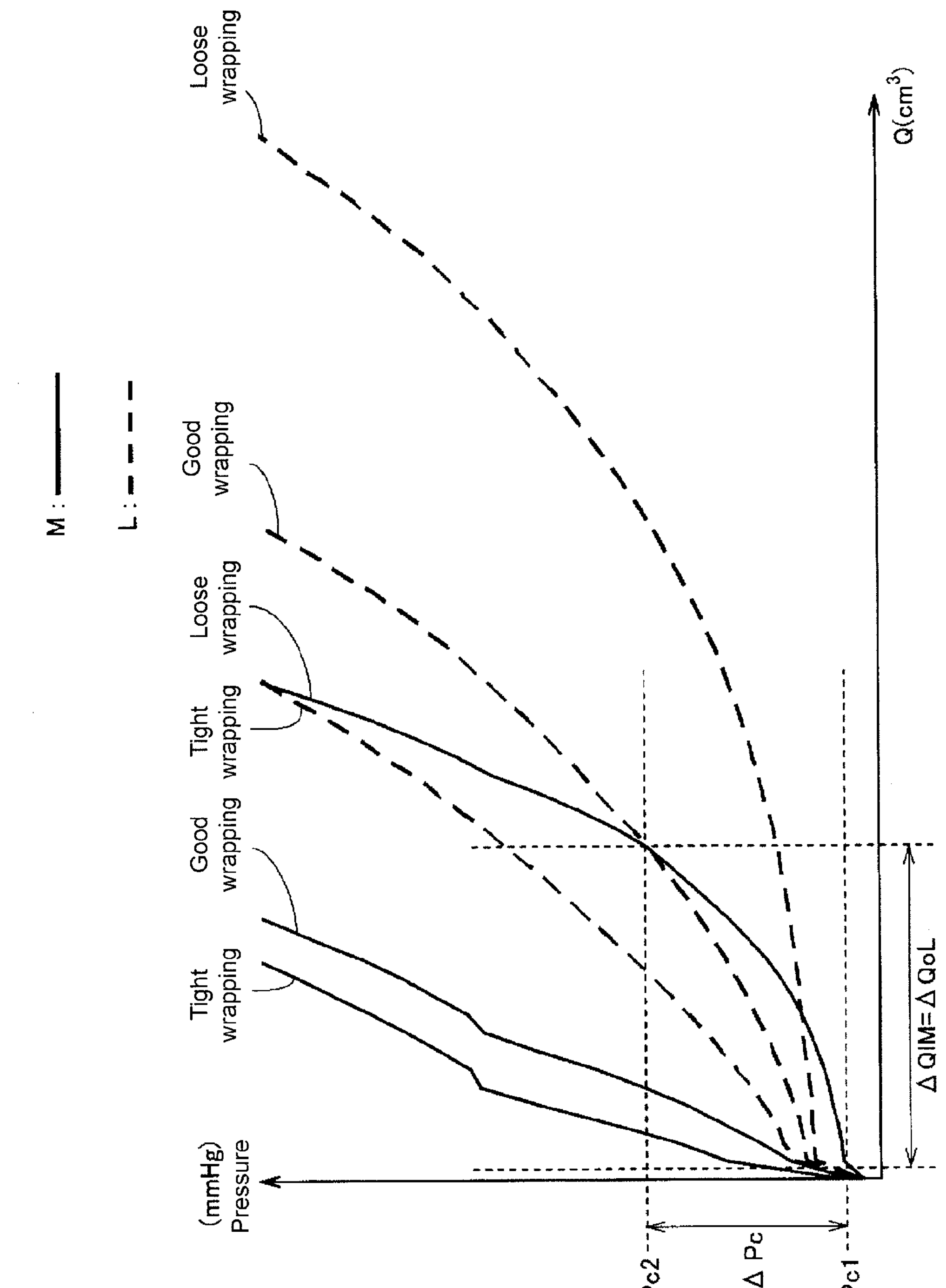
FIG. 22 is a view showing the cuff pressure-volume change relationship according to the wrapping strength when the measurement condition is the arm circumferential length.

The inventors acquired the cuff pressure-volume change relationship according to the wrapping strength of the cuff 20 when the arm circumferential length is the measurement condition as shown in FIG. 22 through experiments. The fluid amount supplied to the cuff 20 to change the cuff pressure is shown on the horizontal axis of the graph of FIG. 22, and the cuff pressure is shown on the vertical axis. In FIG. 22, a solid line graph shows the cuff pressure-volume change relationship according to the wrapping strength when the arm circumferential length is M, and the broken line graph shows the cuff pressure-volume change relationship according to the wrapping strength when the arm circumferential length is L. The arm circumferential length is in a relationship of M<L.

With reference to FIG. 22, the fluid amount to be supplied for the cuff pressure to change by ΔPc is ΔQ1M if the arm circumferential length is M and the wrapping is "loose", LQoL if the arm circumferential length is L and the wrapping is "good", where the relationship of ΔQ1M=ΔQoL is shown. According to FIG. 22, the change in cuff pressure differs depending on the measurement condition, and hence, the threshold value for detection or the values of Pc1 and Pc2 for determining ΔPc need to be changed according to the measurement condition in order to accurately detect the wrapping strength of the cuff 20 according to the cuff pressure-volume change relationship.

(Detection Process of Wrapping Strength)

Figure 23:
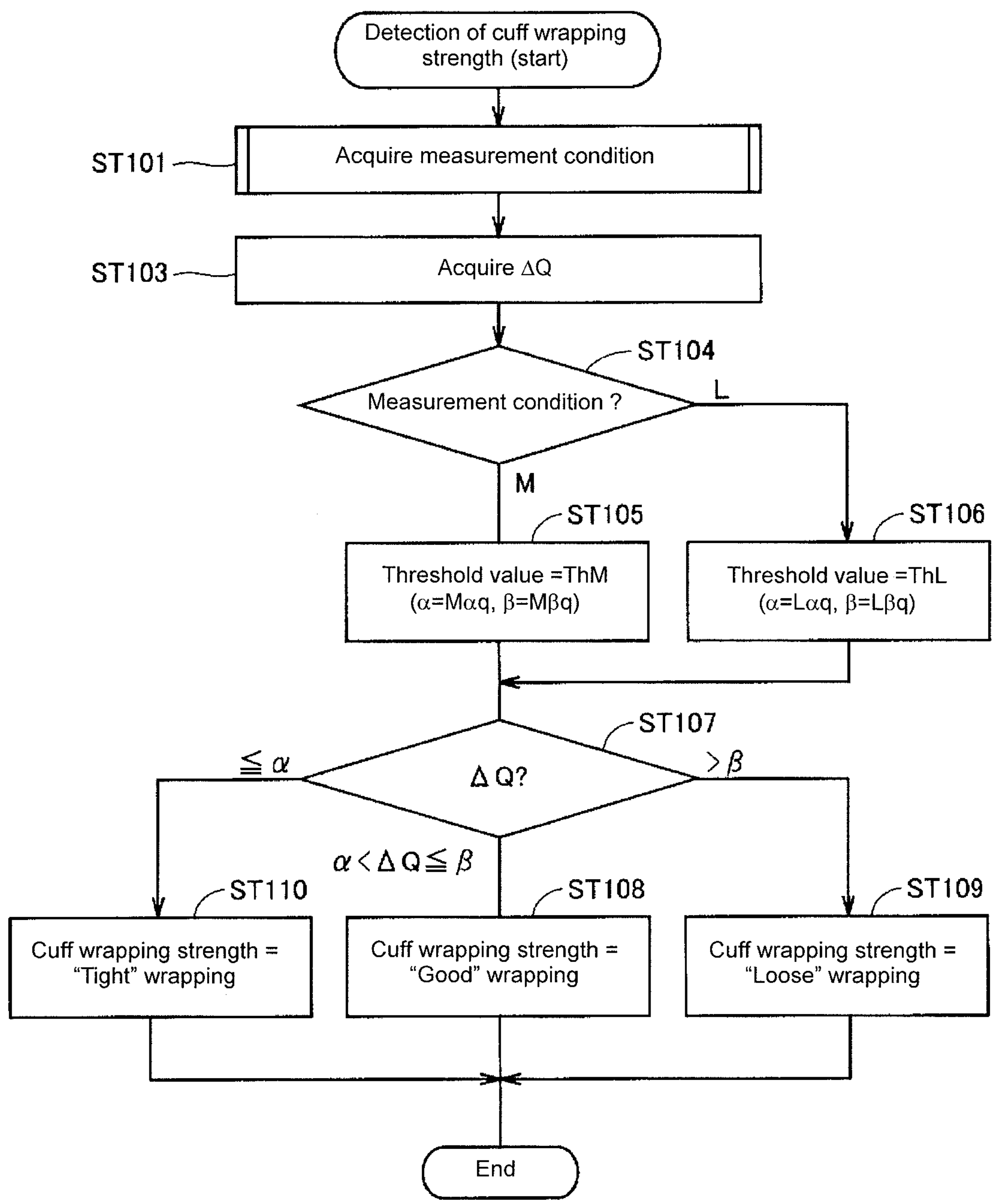
FIG. 23 is a flowchart of a first procedure of the wrapping strength detection according to the second embodiment.

A first procedure of the wrapping strength detection based on the concept of detection described above will be described with reference to the flowchart of FIG. 23. The flowchart of FIG. 23 shows the detailed process of step ST6 of FIG. 20.

In the first procedure, the values of the pressures Pc1 and Pc2 for detecting the cuff pressure ΔPc are fixed predetermined values. The fluid amount ΔQ corresponding to the change in cuff pressure of ΔPc is detected, the detected fluid amount ΔQ and the threshold value variably determined in correspondence with the measurement condition are compared, and the wrapping strength is detected based on the comparison result.

First, the measurement condition detecting portion 132 acquires the measurement condition (step ST101). The acquisition of the measurement condition will be described later. The measurement condition to be acquired is the arm circumferential length. The data of the acquired arm circumferential length is provided to the threshold value detecting part 144.

The cuff pressure signal detected by the pressure detection unit 101 is provided to the cuff pressure zone determining part 140. The cuff pressure zone determining part 140 compares the input cuff pressure signal and the values Pc1 and Pc2 of the cuff pressure read from the memory 48, detects a period (i.e., period corresponding to ΔPc) in which the cuff pressure changes from Pc1 to PC2 based on the comparison result, and outputs a detection signal indicating the period of ΔPc to the flow rate detecting part 145. The flow rate detecting part 145 detects the fluid amount (ΔQ) that flowed into the cuff 20 in the period corresponding to ΔPc based on the flow rate detected by the flow rate sensor 44 based on the detection signal input from the cuff pressure zone determining part 140 (step ST103). The fluid amount (ΔQ) supplied to the cuff 20 to change the cuff pressure by ΔPc is thereby detected.

The threshold value detecting part 144 determines the threshold value of ΔQ for detecting the wrapping strength of the cuff 20 so as to differ according to the input measurement condition (arm circumferential length herein) (steps ST104 to ST106). Specifically, the threshold value detecting part 144 searches the table 395 of the memory 48 through the memory access unit 150 based on the input arm circumferential length. As a result of the search, the data 39L corresponding to the data 39K indicating the input arm circumferential length is read out. The threshold value indicated by the read data 39L is set to temporary variables α and β. Specifically, if the arm circumferential length is M ("M" in step ST104), the threshold values Mαq and Mβq indicated by the threshold value ThM of the read data 39L are set for the variables α and β, respectively, (step ST105). If the arm circumferential length is L ("L" in step ST104), the threshold values Lαq and Lβq indicated by the threshold value ThL of the read data 39L are set for the variables α and β, respectively, (step ST106).

Thereafter, the wrapping strength detecting portion 134 compares the fluid amount (ΔQ) detected in step ST103 and the values of the variables α and β indicating the determined threshold values, and detects the wrapping strength of the cuff 20 based on the comparison result (steps ST107 to ST109). Specifically, the wrapping strength is detected as "tight" wrapping when determined as (ΔQ≤α) based on the comparison result, the wrapping strength is detected as "good" wrapping when determined as (α<ΔQ≤β) based on the comparison result, and the wrapping strength is detected as "loose" wrapping when determined as (ΔQ>β) based on the comparison result.

Figure 24:
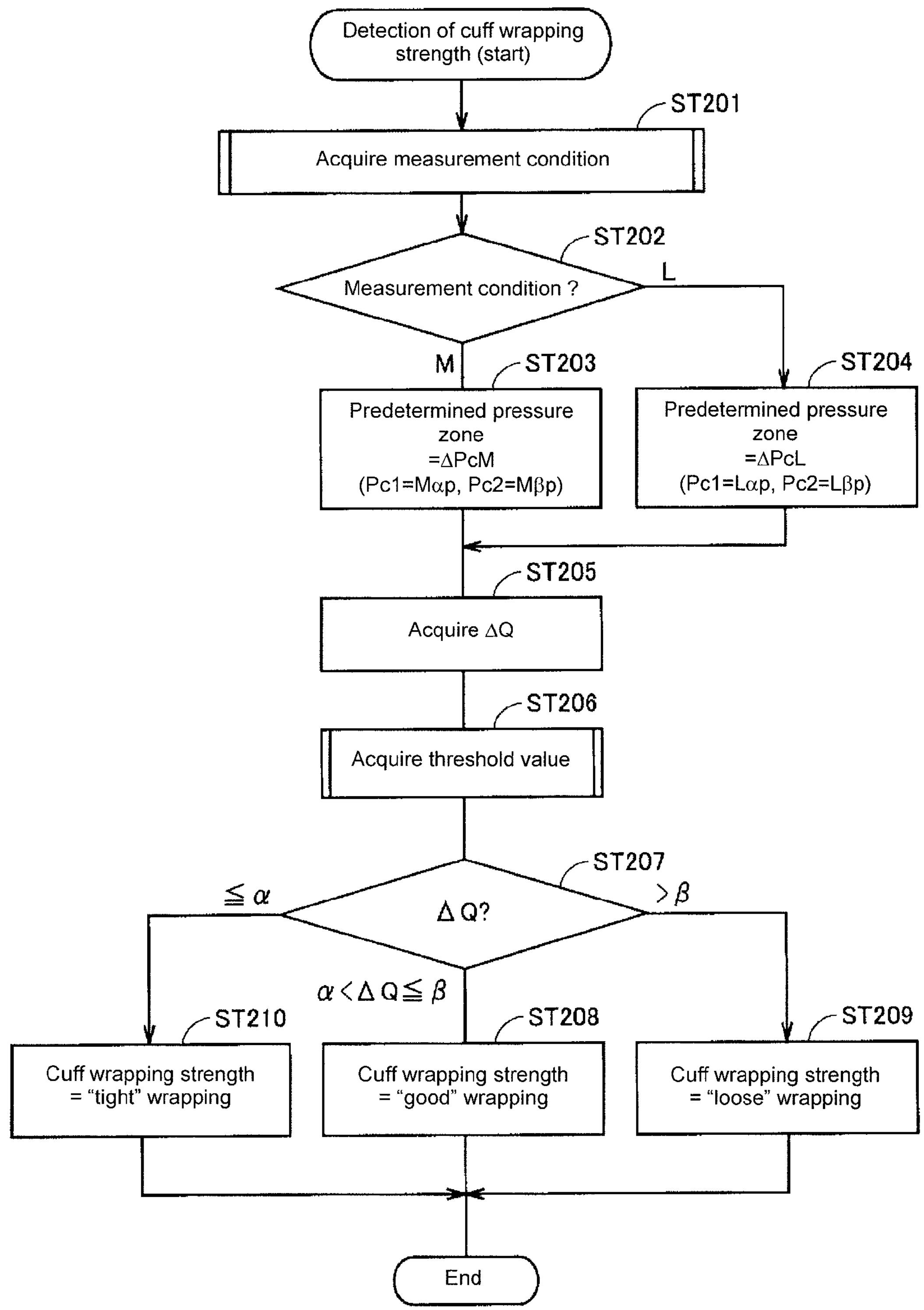
FIG. 24 is a flowchart of a second procedure of the wrapping strength detection according to the second embodiment.

A second procedure will now be described. The second procedure of the detection of the wrapping strength based on the concept of detection is shown in the flowchart of FIG. 24. The flowchart of FIG. 24 shows the detailed process of step ST6 of FIG. 20.

The second procedure changes the values of the pressures Pc1 and Pc2 for detecting the cuff pressure ΔPc so as to become values corresponding to the measurement condition. The fluid amount ΔQ corresponding to the cuff pressure change of ΔPc is detected, the detected fluid amount ΔQ and a predetermined threshold value are compared, and the wrapping strength is detected based on the comparison result. In the second procedure, the values of the pressures Pc1 and Pc2 for detecting ΔPc are changed to become values corresponding to the measurement condition.

First, the measurement condition detecting portion 132 acquires the measurement condition (step S201). The acquisition of the measurement condition will be described later.

The measurement condition to be acquired is the arm circumferential length. The data of the acquired arm circumferential length is provided to the cuff pressure zone determining part 140.

The cuff pressure zone determining part 140 determines the zone for detecting ΔPc so as to differ according to the input measurement condition (arm circumferential length herein) (steps ST202 to ST204). Specifically, the cuff pressure zone determining part 140 searches the table 396 of the memory 48 through the memory access unit 150 based on the input arm circumferential length. As a result of the search, the data 39M corresponding to the data 39K indicating the input arm circumferential length is read out. The threshold value indicated by the read data 39M is set to temporary variables Pc1 and Pc2. Specifically, if the arm circumferential length is M ("M" in step ST202), the threshold values Mαp and Mβp indicated by the threshold value ΔPcM of the read data 39M are set for the variables Pc1 and Pc2 (step ST203). If the arm circumferential length is L ("L" in step ST202), the threshold values Lap and Op indicated by the threshold value ΔPcL of the read data 39M are set for the variables Pc1 and Pc2 (step ST204).

The cuff pressure signal detected by the pressure detection unit 101 is provided to the cuff pressure zone determining part 140. The cuff pressure zone determining part 140 compares the input cuff pressure signal and the values of the variables Pc1 and Pc2, detects the period (i.e., period corresponding to ΔPc) in which the cuff pressure changes from Pc1 to Pc2 based on the comparison result, and outputs a detection signal indicating the period of ΔPc to the flow rate detecting part 145. The flow rate detecting part 145 detects the fluid amount (ΔQ) that flowed into the cuff 20 in the period corresponding to ΔPc based on the detection signal from the flow rate sensor 44 based on the detection signal input from the cuff pressure zone determining part 140 (step ST205). The fluid amount (ΔQ) supplied to the cuff 20 to change the cuff pressure by ΔPc is thereby detected.

Subsequently, the threshold value detecting part 144 determines the threshold value of ΔQ for detecting the wrapping strength of the cuff 20 (step ST206). The values of the variables α and β are thereby determined.

Thereafter, the wrapping strength detecting portion 134 compares the fluid amount (ΔQ) detected in step ST205 and the values of the variables α and β indicating the threshold value determined in step ST206, and detects the wrapping strength of the cuff 20 based on the comparison result, similar to steps ST107 to ST110 (steps ST207 to ST210).

Here the displacement (ΔQ) of the fluid amount Q corresponding to the value of the range (i.e., ΔPc) of the value of the cuff pressure is detected as shown in the graph of FIG. 22, but the displacement (ΔPc) of the cuff pressure corresponding to the value of the range (i.e., ΔQ) of the value of the fluid amount may be detected.

(Detection of Measurement Condition)

In step ST101 or ST201, when the person to be measured operates the switch 41F, the measurement condition detecting portion 132 inputs the measurement condition in accordance with the operation. The method of acquiring the measurement condition is not limited thereto, and the following methods may be adopted.

The measurement condition may be stored in advance in the external memory 47 or the memory on the network (not shown), and the measurement condition detecting portion 132 may read the measurement condition from the memory through the I/F 46.

If the measurement condition is indicated by the characteristics of the person to be measured or the characteristics of the cuff 20, the information of the measurement condition is stored in advance in the memory 48 or the external memory 47 in association with each person to be measured. When the switch 41B is operated at the time of the blood pressure measurement and the person to be measured is selected, the measurement condition detecting portion 132 may read out the information of the measurement condition associated with the selected person to be measured from the memory. A sensor for detecting the cuff type may be arranged at the connecting portion of the cuff 20 and the blood pressure measurement device 1A, the type of cuff 20 may be detected by the sensor when the cuff 20 is connected to the blood pressure measurement device 1A, and the information of the measurement condition associated with the detected cuff type may be read out from the memory 48.

If the measurement condition is indicated by the properties of the pressurization and depressurization mechanisms including the pump 33 and the valve 34, the data of the properties are stored in the memory 48 as measurement condition at the time of factory shipment. The measurement condition detecting portion 132 may read out the measurement condition from the memory 48 at the time of the blood pressure measurement.

If the measurement condition indicates the environmental condition at the time of the blood pressure measurement, the measurement condition detecting portion 132 may acquire the measurement condition based on the output of the temperature sensor 49, the humidity sensor 50, the air pressure sensor (not shown) and the like of the blood pressure measurement device 1A at the time of the blood pressure measurement.

If the measurement condition is the arm circumferential length, the measurement condition can be detected in the following manner. The cuff pressure is indicated on the vertical axis of the graph of FIG. 25 and the fluid amount is indicated on the horizontal axis. According to the experiments conducted by the inventors, the fluid amount ΔQ required for the cuff pressure to change by ΔPc changes according to the circumferential length of the measurement site regardless of the wrapping strength of the cuff 20 when the cuff pressure is greater than or equal to a certain value (e.g., greater than or equal to 20 mmHg) in the relationship of the cuff pressure and the fluid amount of FIG. 25. Therefore, the measurement condition can be detected by detecting the fluid amount ΔQ.

Specifically, the change (ΔQ) of the fluid amount detected in the process of the cuff pressure changing from PC3 (≥20 mmHg) to Pc4 (>Pc3) is detected as ΔQtM, ΔQoM and ΔQlM for the case of "tight" wrapping, "good" wrapping", and "loose" wrapping, respectively, when the arm circumferential length is M. Similarly, when the arm circumferential length is L, ΔQtL, ΔQoL and ΔQlL are detected for the case of "tight" wrapping, "good" wrapping", and "loose" wrapping, respectively. As illustrated, ΔQtM, ΔQoM and ΔQlM indicate substantially the same value ΔQM, and ΔQtL, ΔQoL and ΔQlL indicate substantially the same value ΔQL.

Therefore, the value of ΔQM is stored in advance as the data 39N in association with the arm circumferential length M of the data 39P in the table 397 of the memory 48, and the value of ΔQL is stored in advance as the data 39N in association with the arm circumferential length L. At the time of measurement, the flow rate detecting part 145 detects the fluid amount (ΔQ) while the cuff pressure changes from Pc3 to Pc4. The measurement condition detecting portion 132 searches the table 397 of the memory 48 based on the detected fluid amount. The data of the arm circumferential length indicated by the data 39P associated with the fluid amount of the data 39N that matches the detected fluid amount is read out based on the search result. The measurement condition is thereby detected.

Figure 25:
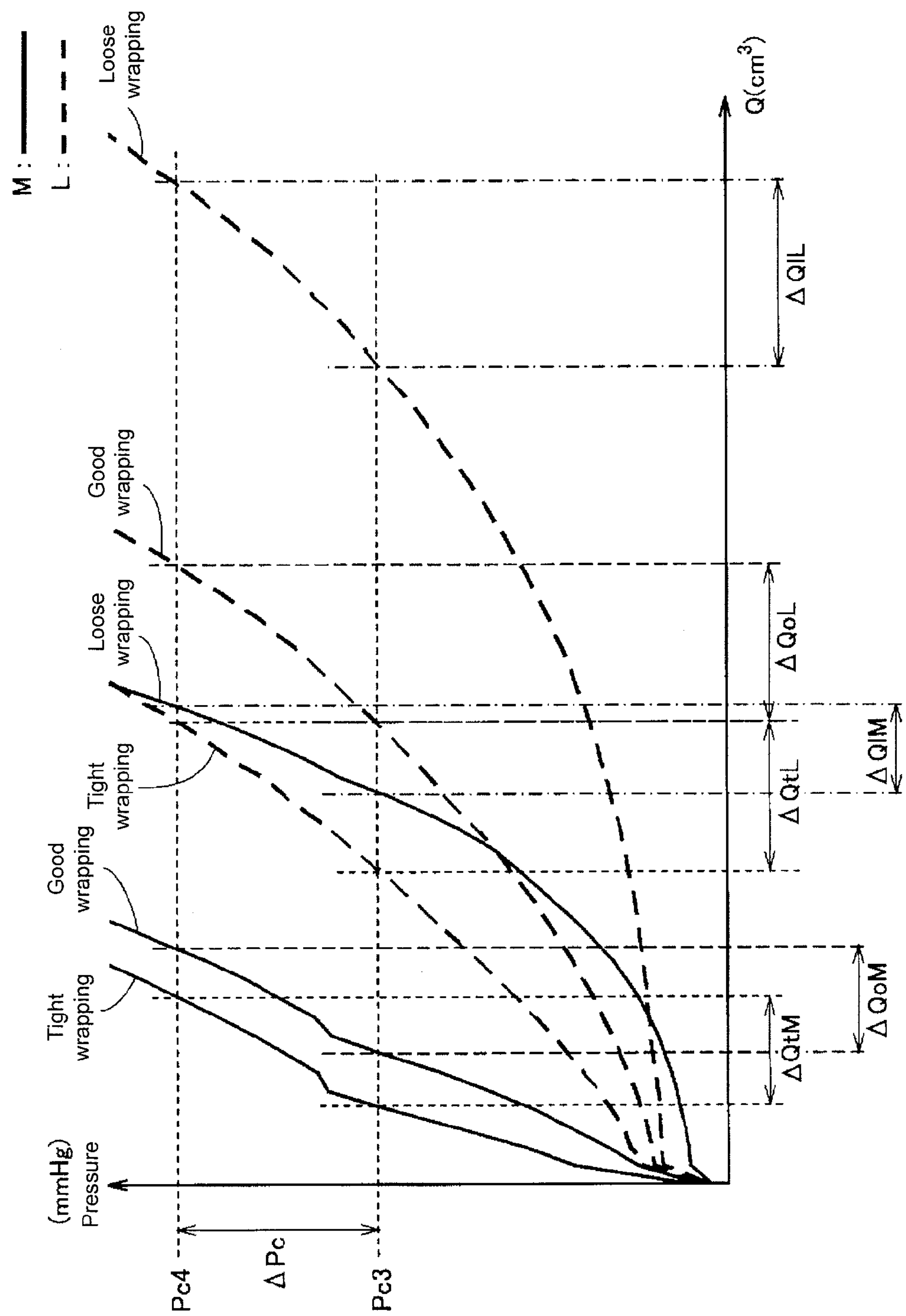
FIG. 25 is a view showing a relationship of the cuff pressure and the fluid amount.

The size (S (small), M (medium), L (large)) of the cuff 20 may be detected as the measurement condition using the same method as that described in FIG. 25.

The measurement condition acquired by the measurement condition detecting portion 132 is recorded in association with the blood pressure measurement result or the like in the recording table 394 (see FIG. 18). The measurement condition may be stored in the external memory 47 or may be displayed on the display unit 40.

(Display Example)

The information of the wrapping strength detected by the wrapping strength detecting portion 134 is output to outside. The display by the display unit 40 will be described as one mode of output. The display unit 40 includes an LCD (Liquid Crystal Display), for instance.

Figure 26:
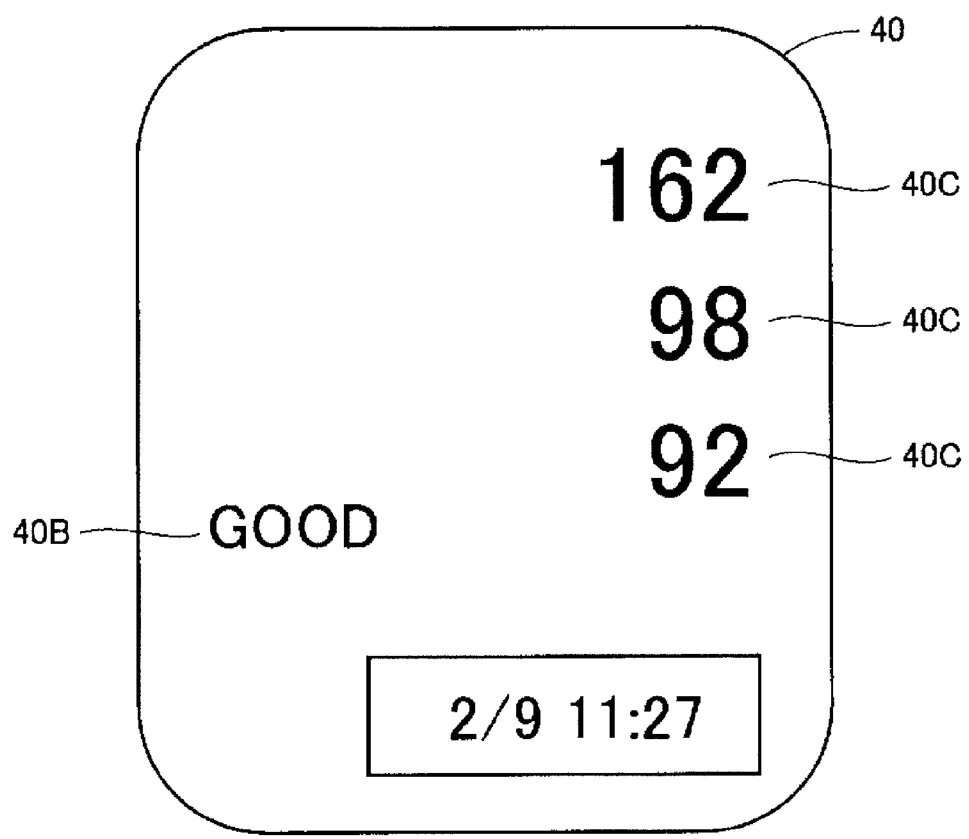
FIG. 26 is a view showing one example of a display according to the second embodiment.

FIG. 26 shows a display example of the measurement result by the blood pressure measurement device 1A. With reference to FIG. 26, data 40B of the detected wrapping strength, data 40C including the maximum blood pressure, the minimum blood pressure, and the pulse rate, and the data of the measurement date and time, and the like are displayed on the same screen as measurement results on the display unit 40 by the display control unit 160. In FIG. 26, the character "GOOD" is displayed indicating that the wrapping strength is appropriate ("good" wrapping) by the data 40B.

The display mode is not limited to FIG. 26, and may be as follows. For instance, if the wrapping strength is inappropriate ("tight" wrapping or "loose" wrapping), the character "TIGHT" or "LOOSE" may be displayed by the data 40B. When the wrapping strength is inappropriate, a message urging rewrapping, information for guiding the appropriate wrapping method, and the like may be displayed with the data 40B. The message or guide information may be displayed on the same screen as the display screen of the data 40B or may be displayed on a different screen.

The wrapping strength is not limited to the display by the characters such as the data 40B, and the wrapping strength may be displayed in a step wise manner with an indicator.

After outputting the wrapping strength, the blood pressure measurement may be paused or terminated depending on the detected wrapping strength. The blood pressure measurement can thus be restarted after the person to be measured rewraps the cuff 20 on the measurement site.

The measurement result output to the display unit 40 includes past measurement data read from the recording table 394 or the data measured immediately before.

The medium for outputting the wrapping strength is not limited to the LCD of the display unit 40, and may be a light emitting medium such as LED (Light Emitting Diode), an audio output medium such as a buzzer or a speaker, a medium for generating vibration such as a vibration motor, and the like.

Figure 27:
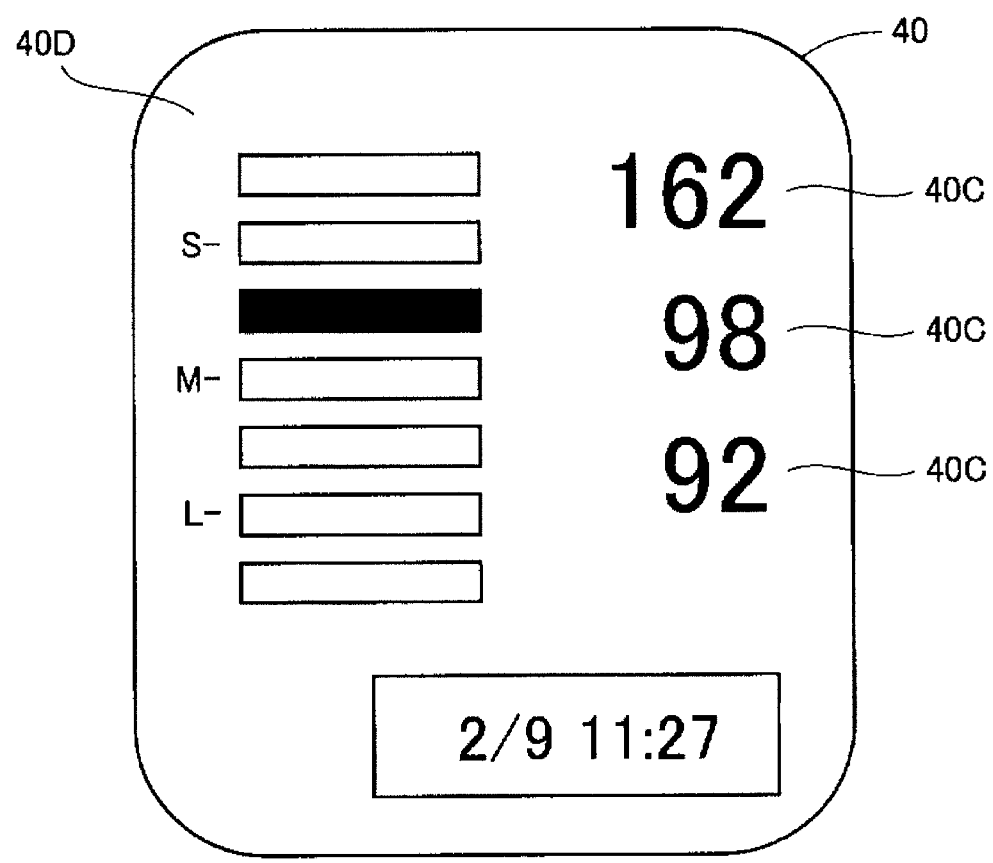
FIG. 27 is a view showing another example of a display according to the second embodiment.

In FIG. 26, only the detected wrapping strength is output but the wrapping strength and the measurement condition may be output as in FIG. 27.

In FIG. 27, the data 40D of the wrapping strength is displayed with the data 40C of the blood pressure measurement. The size (S, M, L) of the cuff 20 serving as the measurement condition, and the wrapping strength detected according to the measurement condition are displayed by the data 40D. The threshold value for the cuff wrapping strength detection differs according to the size (measurement condition) of the cuff 20 under normal circumstances, but the data 40D of FIG. 27 shows the wrapping strength detected when the threshold value is constant regardless of the size. The data 40D includes a pattern of an indicator in which a plurality of square pictographs are continued in a line, and a character indicating the size "S", "M", "L". The character "S", "M", "L" is assigned as shown in the figure to the three pictographs of the pictographs of the indicator.

When the detected wrapping strength indicates the appropriate level corresponding to the size of the cuff 20, only the display mode of the pictograph assigned with the character indicating the relevant size of the data 40D is changed from that of other pictographs in the display. For instance, it is lighted, flashed, or color changed. If the pictograph other than the pictograph assigned with the character indicating the size is lighted or flashed, notification is made that the detected wrapping strength is "loose" wrapping or "tight" wrapping. If such display mode is adopted, the measurement condition does not need to be acquired when detecting the cuff wrapping strength (process of step ST101 of FIG. 23 or process of step ST201 of FIG. 24 are not necessary).

(Correction of Blood Pressure Value)

The correcting portion 123 corrects the parameter value for calculating the blood pressure or the blood pressure value itself based on the detected wrapping strength or the measurement condition. This correction may be executed for every blood pressure measurement, or may be executed only when an instruction to correct is made from the operation unit 411.

For instance, in the oscillometric method, the maximum blood pressure and the minimum blood pressure are calculated by multiplying a predetermined ratio to the maximum value of the pulse wave amplitude acquired when the cuff pressure is changed. In other words, they are calculated with the following equations. Here, ax and bx in the equation are constants.

$$\text{Amplitude value of maximum blood pressure} = \text{maximum amplitude value} \times ax \quad (1)$$

$$\text{Amplitude value of minimum blood pressure} = \text{maximum amplitude value} \times bx \quad (2)$$

The blood pressure value is corrected by changing the values of ax and bx in the equation based on the detected wrapping strength or the measurement condition. The correction example is shown with the graph of FIG. 28.

Figure 28:
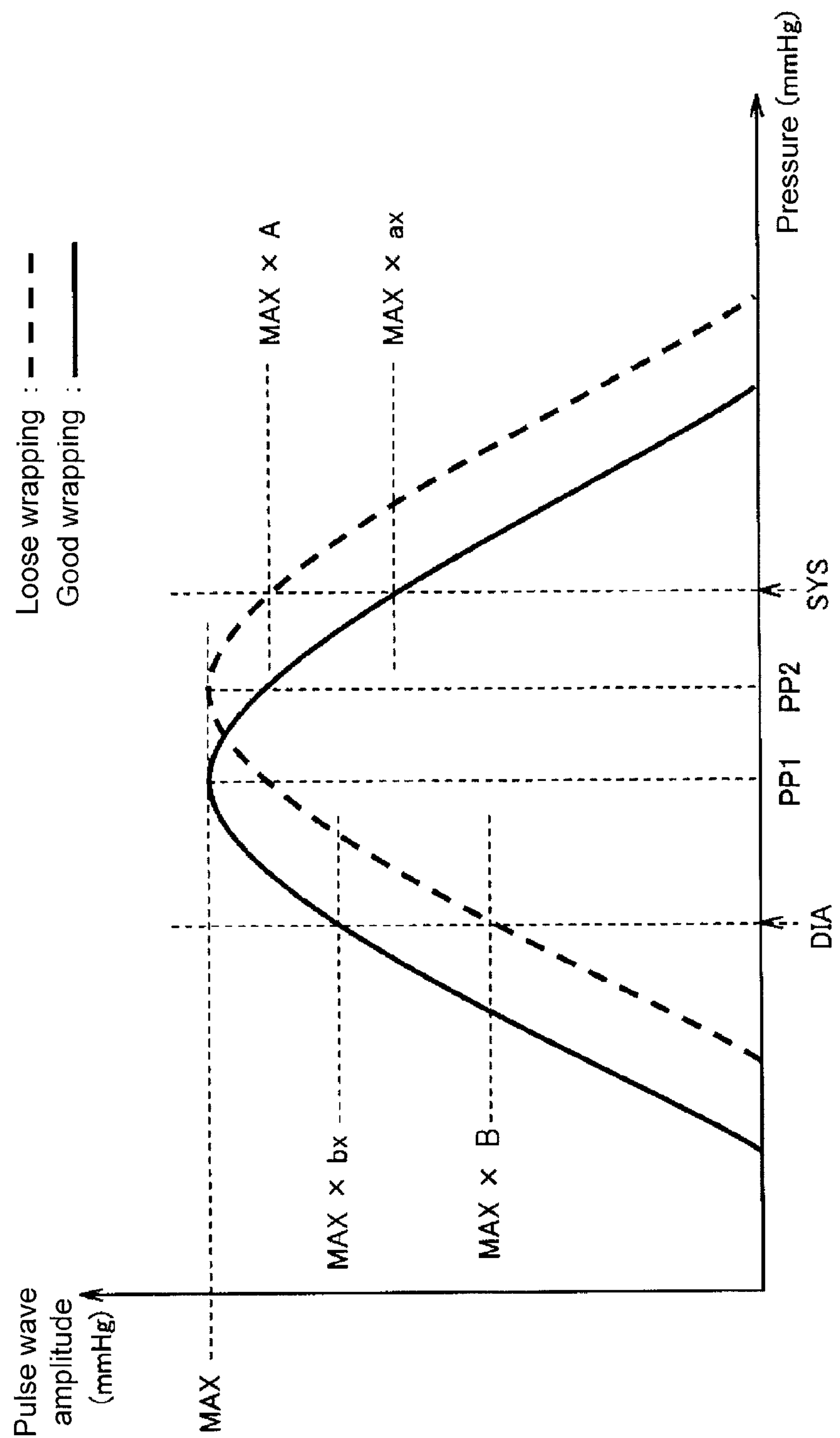
FIG. 28 is a view describing the correction of the blood pressure value according to the second embodiment.

The detected pulse wave amplitude is shown on the vertical axis of the graph of FIG. 28, and the detected cuff pressure is shown on the horizontal axis. When the wrapping strength is "good" wrapping (graph of solid line), the SYS (maximum blood pressure) and the DIA (minimum blood pressure) are calculated based on Equations (1) and (2). On the other hand, in the case of "loose" wrapping (graph of broken line), the maximum value MAX appears at the cuff pressure PP2 higher than the cuff pressure PP1 of "good" wrapping. Therefore, the correction amount detecting part 124 detects the constants A and B corresponding to the difference (PP2−PP1) of cuff pressure. The correcting portion 123 calculates the maximum blood pressure and the minimum blood pressure by multiplying the detected constants A and B to the maximum amplitude value MAX. The corrected blood pressure value is thereby acquired.

If detected as "loose" wrapping, the pressure to be transmitted to the artery attenuates. Thus, the appearance pattern of the pulse wave amplitude shifts to the side of high cuff pressure as shown in FIG. 28. The correction amount detecting part 124 updates the constants ax and bx according to the wrapping strength based on Equations (3) and (4). The correcting portion 123 calculates the blood pressure value using the updated constants as shown in Equations (5) and (6). The corrected blood pressure value is thereby acquired.

$$A=ax\times 1.2 \quad (3)$$

$$B=bx\times 0.7 \quad (4)$$

$$\text{Amplitude value of maximum blood pressure}=\text{maximum amplitude value}\times A \quad (5)$$

$$\text{Amplitude value of minimum blood pressure}=\text{maximum amplitude value}\times B \quad (6)$$

The correction amount is represented with a ratio in Equations (3) and (4), but the correction amount may be represented with an offset as shown in Equations (7) and (8).

$$A=ax+0.2 \quad (7)$$

$$B=bx-0.3 \quad (8)$$

The correction amount is a fixed value in Equations (3), (4), (7), and (8), but the correction amount may be changed according to the wrapping strength because the pressure to be transmitted to the artery tends to attenuate as the wrapping strength becomes "looser".

When correcting the blood pressure value, the blood pressure values determined assuming the wrapping strength is "good" (this is referred to as temporary maximum blood pressure and temporary minimum blood pressure) are uniformly acquired independent from the wrapping strength or the measurement condition. Thereafter, the correcting portion 123 corrects the temporary blood pressure values based on the Equations (9) and (10) based on the wrapping strength or the measurement condition. Here, γ and η in the equations are constants.

$$\text{maximum blood pressure value}=\text{temporary maximum blood pressure value}\times\gamma \quad (9)$$

$$\text{minimum blood pressure value}=\text{temporary minimum blood pressure value}\times\eta \quad (10)$$

The correction of the temporary blood pressure values is not limited to the method of multiplying the ratio as in Equations (9) and (10), and may be a method of adding or subtracting an offset. The correction amount (ratio and offset) may be changed according to the wrapping strength.

In either of correction methods described above, the correction value is recorded in advance in the memory 48 in the form of a table or a mathematical formula, and appropriately read out from the memory 48 by the correction amount detecting part 124 at the time of calculating the blood pressure.

(Gain Determination According to Measurement Condition)

The gain data determined by the gain determining portion 112 is changed according to the wrapping strength or the measurement condition.

The pressure adjustment unit 111 typically variably controls the gain data according to the cuff pressure detected by the pressure detection unit 101, i.e., carries out a so-called feedback control. However, in the feedback control, the parameter value referenced by the gain determining portion 112 to determine the gain data is set to a safe value to avoid excessive control (e.g., rotation of pump 33 becomes high speed in excess) when the arm circumferential length or the size of the cuff 20 is unknown. As a result, the time for the control system to stabilize is required and it becomes difficult to be sufficiently stabilized.

In the present embodiment, the gain determining portion 112 changes the gain data based on the wrapping strength or the measurement condition (arm circumferential length or size of cuff 20) detected by the wrapping strength/measurement condition detection unit 130A. The cuff pressure can be optimally pressurization/depressurization controlled because the displacement (ΔQ) of the fluid amount per predetermined time in the cuff 20 at the time of pressurization/depressurization can be increased and decreased according to the magnitude of the size of the cuff 20.

In the present embodiment, the cuff pressure-volume change relationship obtained in the process of pressurizing the cuff pressure is used, but the cuff pressure-volume change relationship obtained in the process of depressurizing may be used.

Third Embodiment

In a third embodiment, a configuration combining the first embodiment and the second embodiment is shown.

Figure 29:
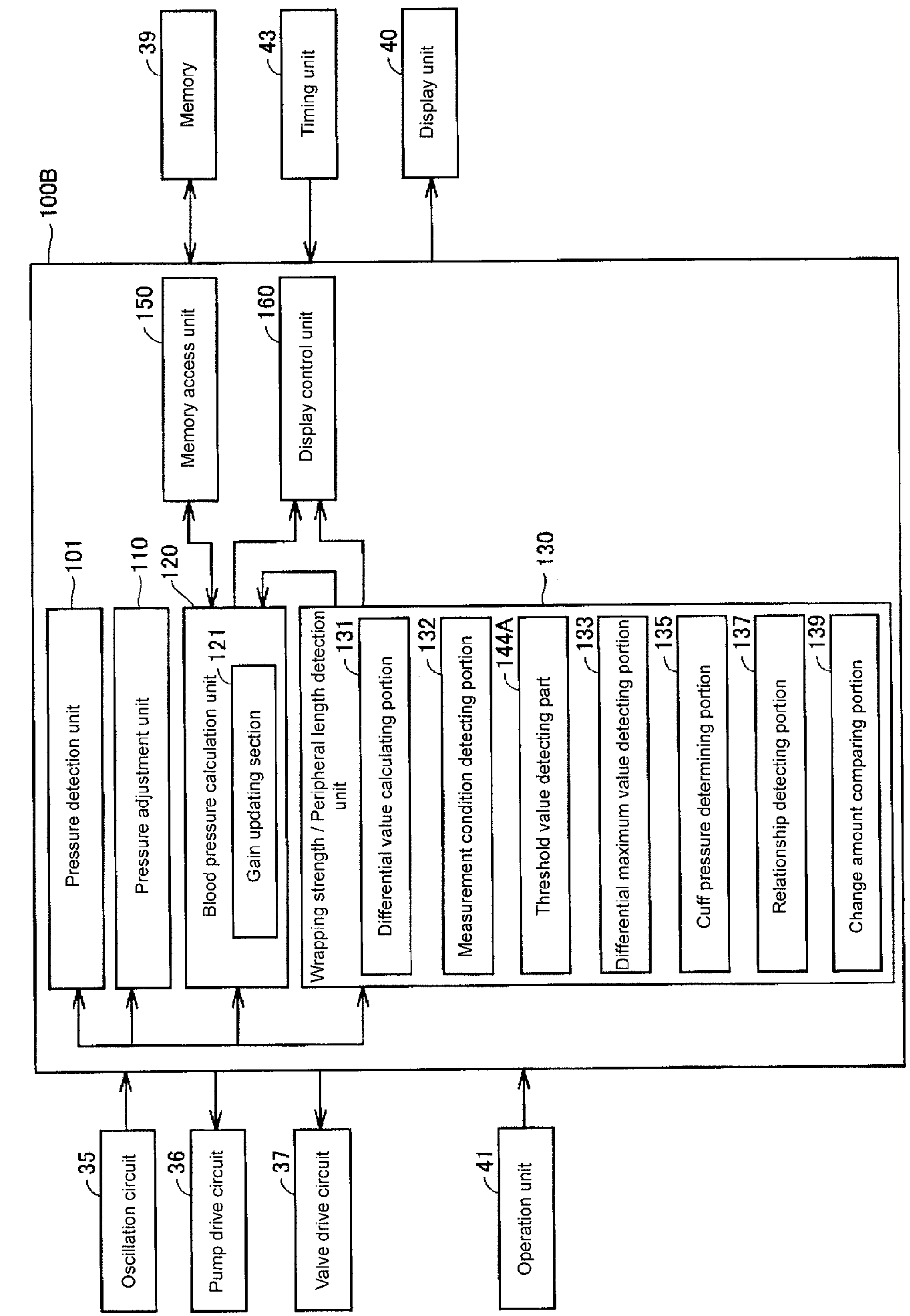
FIG. 29 is a view showing a function configuration according to a third embodiment.

In FIG. 29, peripheral circuits related to a CPU 100B according to a blood pressure measurement device of the third embodiment are shown. The CPU 100B of FIG. 29 is different compared to the CPU 100 of FIG. 3 in that the wrapping strength/circumferential length detection unit 130 additionally includes a measurement condition detecting portion 132 and a threshold value detecting part 144A in the configuration of FIG. 3.

The slope of the graph of FIG. 8 differs according to the measurement condition (size of cuff 20, arm circumferential length, etc.) even if the discharge flow rate per unit time of the pump 33 is constant and the wrapping strength is the same, as described in the second embodiment. Therefore, in order to accurately detect the wrapping strength, the values of the pressures P1, P2, P3, and P4 shown in the first embodiment are desirably controlled to take different values by the threshold value detecting part 144A according to the measurement condition detected by the measurement condition detecting portion 132.

In the present embodiment, the values of the pressures P1, P2, P3 and P4 are detected through experiments and stored in advance in correspondence with the respective measurement conditions in the memory 39. At the time of the measurement, the threshold value detecting part 144A searches the memory 39 based on the detected measurement condition, and reads out the values of the corresponding pressures P1, P2, P3, and P4. The values of the optimum pressures P1, P2, P3, and P4 corresponding to the measurement condition thus can be acquired, and the wrapping strength can be more accurately detected.

Fourth Embodiment

A blood pressure measurement device according to the present embodiment pauses the blood pressure measurement operation after detecting the wrapping strength of the cuff 20.

Figure 30:
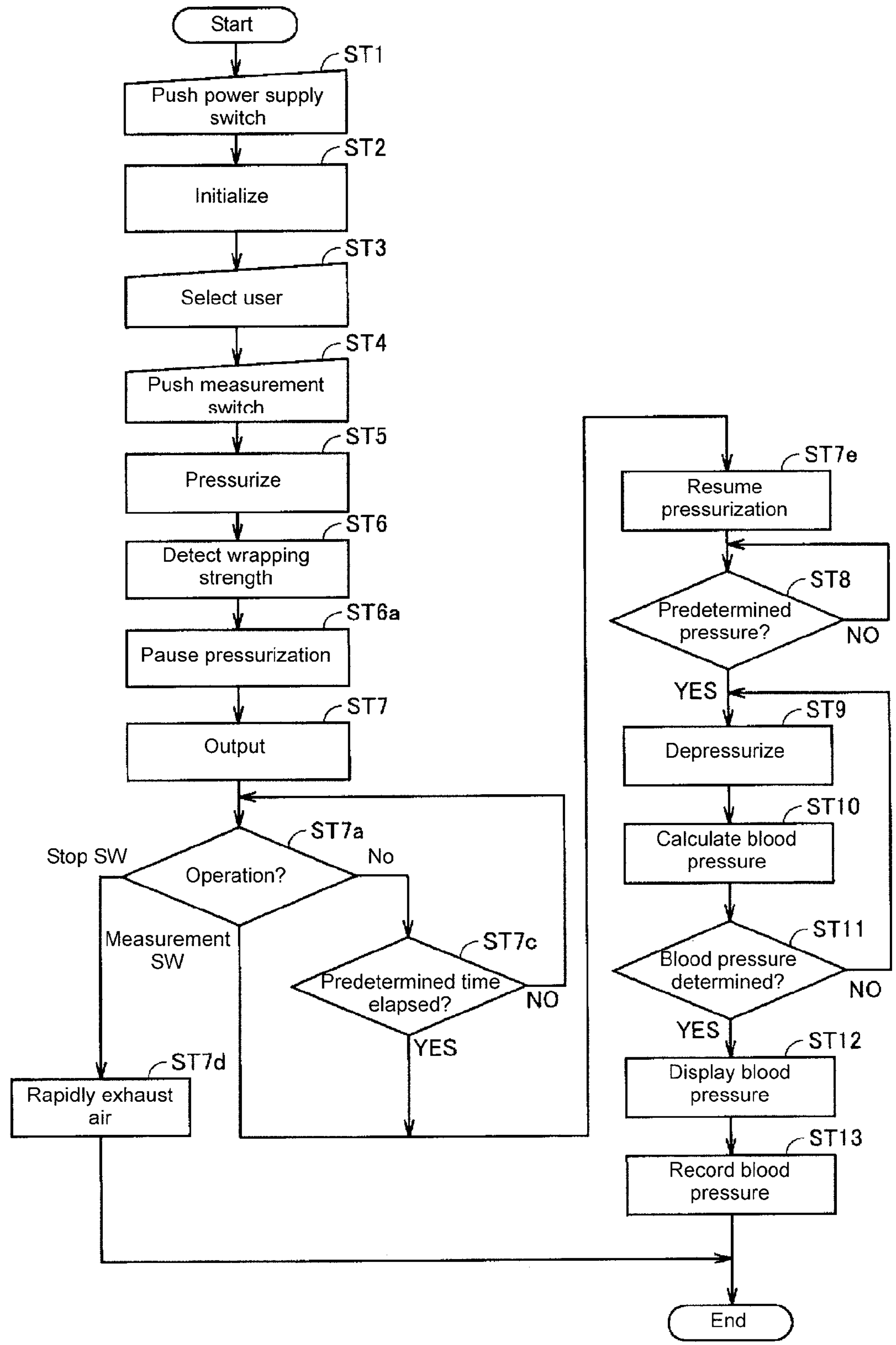
FIG. 30 is a flowchart of a blood pressure measurement process according to a fourth embodiment.

FIG. 30 is a process flowchart of the blood pressure measurement according to the fourth embodiment. In this flowchart, the processes of steps ST6*a* and 7*a* to 7*e* are added to the flowchart of FIG. 20. Therefore, the added processes will be described in detail, and other processes will be briefly described. It is assumed that the person to be measured wrapped the cuff 20 around the measurement site in advance in carrying out the measurement.

After the processes of steps ST1 to ST6 are executed and the wrapping strength is detected similarly to FIG. 20, the pressure adjustment unit 111 pauses the pressurization operation on the cuff 20 (step ST6*a*) and thereafter, the display control unit 160 outputs the detected wrapping strength to the display unit 40 (step ST7). The wrapping strength may be output after pausing the pressurization operation.

The blood pressure measurement operation is paused due to the pausing of the pressurization operation. The person to be measured checks the output wrapping strength. If detected as “loose” wrapping or “tight” wrapping, the person to be measured operates the switch 41D (“stop SW” in step ST7a), and the pressure adjustment unit 111 performs a control to open the valve 34 in response to the operation. The air is then rapidly exhausted from the cuff 20 (step ST7d). As a result, the blood pressure measurement is canceled. The person to be measured can again wrap the cuff 20 around the measurement site to restart the blood pressure measurement.

If detected that the person to be measured has not operated the operation unit 411 at all even after an elapse of a predetermined time (e.g., 30 seconds) with the pressurization operation in the pause state (“no” in step ST7a, YES in step ST7c), the pressurization operation is resumed (step ST7e) and the process proceeds to the measurement process (steps ST8 to ST13). The process may proceed to the measurement process (steps ST7e, ST8 to ST13) if detected that the person to be measured performed a predetermined operation (e.g., again operate switch 41C) within a predetermined time from when the pressurization operation is paused (“measurement SW” in step ST7a).

Fifth Embodiment

A blood pressure measurement device according to the present embodiment includes an operation unit operated to instruct start of detection of the wrapping strength of the cuff 20. In the operation of the blood pressure measurement, the wrapping strength of the cuff 20 is detected when the operation of the relevant operation unit is detected.

Figure 31:
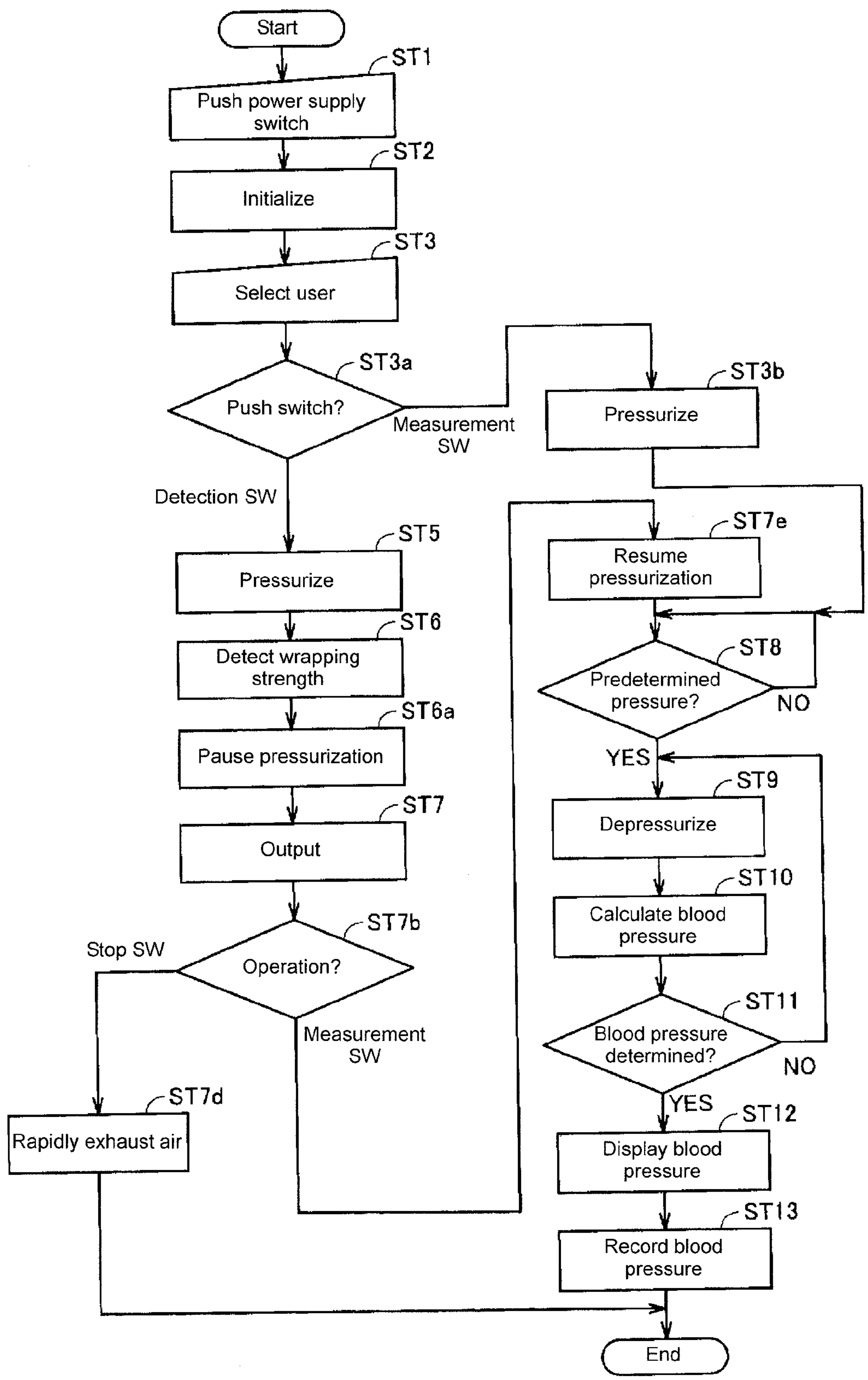
FIG. 31 is a flowchart of a blood pressure measurement process according to a fifth embodiment.

FIG. 31 is a process flowchart of the blood pressure measurement according to the fifth embodiment. In this flowchart, the processes of steps ST3a and ST3b as well as ST7b to 7e are added to the flowchart of FIG. 20. Therefore, the added processes will be described in detail, and other processes will be briefly described. It is assumed that the person to be measured wrapped the cuff 20 around the measurement site in advance in carrying out the measurement.

In the present embodiment, the person to be measured operates the switch 41G (see FIG. 17) to instruct the start of detection of the wrapping strength of the cuff 20.

With reference to FIG. 31, when the processes of steps ST1 to ST3 are executed similarly to those in FIG. 20, which switch 41C or 41G the person to be measured operated is detected (step S3a). If the operation of the switch 41G is detected (“detection SW” in step ST3a), the pressure adjustment unit 111 raises the cuff pressure (step ST5), and the wrapping strength of the cuff 20 is detected (step ST6). The pressure adjustment unit 111 pauses the pressurization operation with respect to the cuff 20 (step ST6a), and thereafter, the display control unit 160 outputs the detected wrapping strength to the display unit 40 (step ST7). The wrapping strength may be output after pausing the pressurization operation.

The blood pressure operation is paused due to the pausing of the pressurization operation. The person to be measured checks the output wrapping strength. If detected as “loose” wrapping or “tight” wrapping, the person to be measured operates the switch 41D (“stop SW” in step ST7b), and the pressure adjustment unit 111 performs a control to open the valve 34 in response to the operation. The air is then rapidly exhausted from the cuff 20 (step ST7d). As a result, the blood pressure measurement is canceled. The person to be measured can again wrap the cuff 20 around the measurement site to restart the blood pressure measurement.

If detected that the person to be measured operated the switch 41C after the pressurization operation is paused (“measurement SW” in step ST7b), the pressurization on the cuff 20 is resumed (step ST7e) and the process proceeds to the measurement process (steps ST8 to ST13).

If the operation of the switch 41C is detected instead of the switch 41G (“measurement SW in step ST3a), the detection of the wrapping strength is omitted, and the pressurization with respect to the cuff 20 is started for the blood pressure measurement (step ST3b). The pressurization is continued until the cuff pressure indicates a predetermined pressure (YES in step ST8). Subsequently, the process proceeds to the measurement process (steps ST8 to ST13). In this case, the display and recording of the wrapping strength data are omitted in steps ST12 and ST13.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

Embodiments of the present invention are effective in a blood pressure measurement device of a type in which the cuff is wrapped around the measurement site.

DESCRIPTION OF REFERENCE NUMERALS

110, 111 pressure adjustment unit
120, 122 blood pressure calculation unit
121 gain updating portion
123 correcting portion
124 correction amount detecting part
130 wrapping strength/circumferential length detection unit
131 differential calculating portion
132 measurement condition detecting portion
133 differential maximum value detecting portion
134 wrapping strength detecting portion
135 cuff pressure determining portion
137 relationship detecting portion
139 change amount comparing portion
144 threshold value detecting part
145 flow rate detecting part
391 gain table
130 A wrapping strength/measurement condition detection unit

The invention claimed is:

1. A blood pressure measurement device comprising:

a cuff to be wrapped around a measurement site;

a pressure control unit that controls a cuff pressure in the cuff when the cuff is wrapped around the measurement site;

a pressure detection unit that detects the cuff pressure;

a volume detection unit that detects a volume of the cuff in a process of pressurizing or depressurizing the cuff pressure by the pressure control unit;

a blood pressure calculation unit that calculates a blood pressure value in the process of pressurizing or depressurizing the cuff pressure by the pressure control unit; and a wrapping strength detecting portion that detects a wrapping strength of the cuff with respect to the measurement site, wherein the wrapping strength detecting portion detects, during a change of the cuff pressure in a process of controlling the cuff pressure by pressurization or depressurization by the pressure control unit, the wrapping strength of the cuff based on a pressure-volume change relationship according to a change of the cuff pressure detected in the cuff when the cuff is wrapped around the measurement site and a volume change of the cuff detected by the volume detection unit.

2. The blood pressure measurement device according to claim 1, wherein the wrapping strength detecting portion detects the wrapping strength of the cuff based on the pressure-volume change relationship and a measurement condition, and wherein the pressure-volume change relationship indicates a relationship of an amount of change of the cuff pressure and an amount of change of the volume when at least one of the cuff pressure and the volume detected in the cuff when wrapped around the measurement site is changed a predetermined amount in the process of controlling the pressure by pressurization or depressurization by the pressure control unit.

3. The blood pressure measurement device according to claim 2, wherein the predetermined amount is changed by the pressure control unit based on the measurement condition.

4. The blood pressure measurement device according to claim 2, wherein the measurement condition indicates a circumferential length of the measurement site.

5. The blood pressure measurement device according to claim 2, wherein the measurement condition is a factor that changes the pressure-volume relationship, and wherein the factor indicates at least one selected from the group consisting of a circumferential length of the measurement site, a quality of the measurement site, a size of the cuff, temperature and humidity around the blood pressure measurement device, characteristics of the pressure control unit, and a fluid volume remaining in the cuff at the end of the blood pressure measurement.

6. The blood pressure measurement device according to claim 2 further comprising:

a measurement condition detecting portion that detects the measurement condition based on the pressure-volume change relationship of the cuff.

7. The blood pressure measurement device according to claim 2 further comprising:

a measurement condition detecting portion that detects the measurement condition, wherein the wrapping strength detected by the wrapping strength detecting portion and the measurement condition detected by the measurement condition detecting portion are output in association to each other.

8. The blood pressure measurement device according to claim 2, wherein the blood pressure calculation unit calculates the blood pressure value based on a volume pulse wave signal and a parameter value, and wherein the parameter value is changed based on at least one of the wrapping strength and the measurement condition.

9. The blood pressure measurement device according to claim 8 further comprising:

a memory, wherein a magnitude of an amplitude of the volume pulse wave signal for calculating the blood pressure value is changed by gain data stored in the memory based on the wrapping strength detected by the wrapping strength detecting portion.

10. The blood pressure measurement device according to claim 2, wherein the pressure control unit controls the cuff pressure according to control data, and wherein the control data is changed based on at least one of the wrapping strength and the measurement condition.

11. The blood pressure measurement device according to claim 2, wherein the blood pressure measurement device cancels the blood pressure measurement when the detected wrapping strength does not indicate an appropriate level.

12. The blood pressure measurement device according to claim 2, wherein the blood pressure measurement device pauses the measurement operation of the blood pressure after the wrapping strength of the cuff is detected.

13. The blood pressure measurement device according to claim 1, wherein the wrapping strength detecting portion detects the wrapping strength of the cuff based on a pressure-volume change relationship indicated by a volume change of the cuff detected with the change of the cuff pressure detected in the cuff when wrapped around the measurement site from a first value to a second value and a volume change of the cuff detected with a change from the second value to a third value in a process of controlling the cuff pressure by pressurization or depressurization by the pressure control unit.

14. The blood pressure measurement device according to claim 13, wherein the blood pressure calculation unit calculates the blood pressure value based on a volume pulse wave signal and a parameter value, and wherein the parameter value is changed based on the wrapping strength.

15. The blood pressure measurement device according to claim 14 further comprising:

a memory, wherein a magnitude of an amplitude of the volume pulse wave signal for calculating the blood pressure value is changed by gain data stored in the memory based on the wrapping strength detected by the wrapping strength detecting portion.

16. The blood pressure measurement device according to claim 13, wherein the pressure control unit controls the cuff pressure according to control data, and wherein the control data is changed based on the wrapping strength.

17. The blood pressure measurement device according to claim 1, wherein the pressure control unit comprises a pressure adjustment unit that supplies or discharges fluid of a constant amount per unit time with respect to the cuff to control the cuff pressure, wherein the wrapping strength detecting portion comprises a relationship detecting portion that detects the pressure-volume change relationship, and wherein the relationship detecting portion detects the pressure-volume change relationship based on a relationship of an elapsed time for supplying or discharging the fluid with respect to the cuff by the pressure adjustment unit, and the pressure detected with elapse of time.

18. The blood pressure measurement device according to claim 17, wherein the volume detection unit substitutes the elapsed time with a parameter value for determining the elapsed time.

19. The blood pressure measurement device according to claim 17, wherein the pressure adjustment unit is an actuator comprising a rotation mechanism, and wherein the elapsed time is substituted by a rotation number of the actuator.

20. The blood pressure measurement device according to claim 17, wherein the elapsed time refers to a power amount consumed by the pressure adjustment unit.

21. The blood pressure measurement device according to claim 17, wherein the volume detection unit substitutes the elapsed time with a supply amount or a discharge amount of the fluid.

22. The blood pressure measurement device according to claim 1, wherein the wrapping strength detecting portion detects the wrapping strength of the cuff with respect to the measurement site when a predetermined instruction is made.

* * * * *